(12) United States Patent
Rousseau et al.

(10) Patent No.: US 10,942,368 B2
(45) Date of Patent: Mar. 9, 2021

(54) METHOD FOR DETERMINING AN OPTICAL SYSTEM OF A PROGRESSIVE LENS

(71) Applicant: Essilor International, Charenton-le-Pont (FR)

(72) Inventors: Benjamin Rousseau, Charenton le Pont (FR); Guilhem Escalier, Charenton le Pont (FR); Isabelle Poulain, Charenton le Pont (FR); Juliette Wierzbicki, Charenton le Pont (FR); Laurent Calixte, Charenton le Pont (FR); Nacer Lakhchaf, Charenton le Pont (FR); Sarah Marie, Charenton le Pont (FR); Thierry Bonnin, Charenton le Pont (FR); Valerie Jolivet, Charenton le Pont (FR)

(73) Assignee: Essilor International, Charenton-le-Pont (FR)

( * ) Notice: Subject to any disclaimer, the term of this patent is extended or adjusted under 35 U.S.C. 154(b) by 198 days.

(21) Appl. No.: 15/767,698

(22) PCT Filed: Oct. 11, 2016

(86) PCT No.: PCT/EP2016/074340
§ 371 (c)(1),
(2) Date: Apr. 12, 2018

(87) PCT Pub. No.: WO2017/064060
PCT Pub. Date: Apr. 20, 2017

(65) Prior Publication Data
US 2018/0299694 A1 Oct. 18, 2018

(30) Foreign Application Priority Data

Oct. 15, 2015 (EP) .................................... 15306644
Oct. 15, 2015 (EP) .................................... 15306646
(Continued)

(51) Int. Cl.
*G02C 7/02* (2006.01)
*A61B 3/113* (2006.01)
(Continued)

(52) U.S. Cl.
CPC .............. *G02C 7/027* (2013.01); *A61B 3/113* (2013.01); *G02C 7/025* (2013.01); *G02C 7/065* (2013.01); *G02C 13/003* (2013.01); *G06F 3/013* (2013.01)

(58) Field of Classification Search
CPC ........ G02C 7/065; G02C 7/066; G02C 7/068; G02C 7/063; G02C 7/028
See application file for complete search history.

(56) References Cited

U.S. PATENT DOCUMENTS

2003/0107707 A1 6/2003 Fisher et al.
2007/0229761 A1 10/2007 Gimenez Carol et al.
(Continued)

FOREIGN PATENT DOCUMENTS

EP 1 747 750 A1 1/2007
EP 2 369 403 A1 9/2011
(Continued)

OTHER PUBLICATIONS

International Search Report dated Dec. 23, 2016, in PCT/EP2016/074340, filed Oct. 11, 2016.

*Primary Examiner* — Darryl J Collins
*Assistant Examiner* — Journey F Sumlar
(74) *Attorney, Agent, or Firm* — Oblon, McClelland, Maier & Neustadt, L.L.P.

(57) ABSTRACT

A method for determining an optical system of a personalized progressive lens for a given wearer including: a) providing a mean direction of gaze determined for the wearer in a reference frame tied to the head of the wearer; b) determining a target value for at least one optical design (Continued)

parameter as a function of the mean direction of gaze determined in a); c) calculating the optical system of the progressive lens by an optical optimization procedure on the basis of target values, wherein the target value of each optical design parameter as a function of the mean direction of gaze determined in b) is a target value.

15 Claims, 14 Drawing Sheets

(30) Foreign Application Priority Data

| | | | |
|---|---|---|---|
| Oct. 15, 2015 | (EP) | ...................................... | 15306647 |
| Oct. 15, 2015 | (EP) | ...................................... | 15306655 |
| Nov. 27, 2015 | (EP) | ...................................... | 5306891 |

(51) Int. Cl.
| | |
|---|---|
| *G02C 7/06* | (2006.01) |
| *G02C 13/00* | (2006.01) |
| *G06F 3/01* | (2006.01) |

(56) References Cited

U.S. PATENT DOCUMENTS

| | | |
|---|---|---|
| 2008/0106697 A1 | 5/2008 | Pedrono |
| 2010/0128220 A1 | 5/2010 | Chauveau |
| 2011/0222019 A1 | 9/2011 | Suzuki et al. |

FOREIGN PATENT DOCUMENTS

| | | |
|---|---|---|
| FR | 2 914 173 A1 | 10/2008 |
| WO | WO 01/62139 A1 | 8/2001 |
| WO | WO 2006/027448 A1 | 3/2006 |
| WO | WO 2015/074777 A1 | 5/2015 |

METHOD FOR DETERMINING AN OPTICAL SYSTEM OF A PROGRESSIVE LENS

The present invention relates generally to the field of ophthalmic optics where a lens is intended to equip a frame so as to correct the defects of the vision of a wearer. The present invention envisages more particularly a method for determining an optical system of a progressive lens. Within the framework of the present document a lens intended to equip the frame of a wearer is referred to interchangeably as a "lens" or an "ophthalmic lens". The said progressive lens is in particular defined at least by a fitting cross and is personalized for a given wearer having prescription data, including a prescribed addition. The said method is for example implemented by computing means.

The ever more precise personalization of progressive lenses intended to equip a frame for a given wearer, with a view to correcting his vision, requires increased knowledge of the visual behaviour of the wearer under natural conditions of vision which are representative of the actual use of the said progressive lenses.

In order to take the visual behaviour of a given wearer into account, it is known to determine an optical system of a progressive lens for this wearer by an optical optimization procedure based on target values, where the prescription data are target values of the said calculation and where one or more supplementary target value(s) is (are) introduced into the calculation of the optical system and where each supplementary target value is determined so as to take an optical design parameter into account.

An exemplary calculation of an optical system of a lens by an optical optimization procedure based on target values is described in the following publication: "*Application of optimization in computer-aided ophthalmic lens design*" (P. Allione, F. Ahsbahs and G. Le Saux, in *SPIE* Vol. 3737, *EUROPTO Conference on Design and Engineering of Optical Systems, Berlin*, May 1999), which is incorporated by reference into the present patent application; according to the procedure described in this document, the optimization calculation is performed by virtue of ray tracing algorithms.

Moreover, patent document WO 2015/074777 A1 describes a procedure for calculating an optical system of a lens by an optical optimization procedure based on target values where one or more supplementary target value(s) is (are) introduced into the calculation of the optical system. This document is also incorporated by reference into the present patent application.

There remains nonetheless a constant need to improve progressive lenses; this can be satisfied by taking into account one or more optical design parameter(s) which are of such a nature as to characterize the wearer's visual behaviour in a more precise manner.

To this end, the present invention proposes a method for determining an optical system of a progressive lens defined at least by a fitting cross, the said progressive lens being personalized for a given wearer having prescription data, including a prescribed addition, $ADD_p$, and the said method being implemented by computing means and comprising the following consecutive steps:

a) providing a mean direction of gaze, $DR_m$, determined for the wearer in a reference frame, $R_{CRO}$, tied to the head of the said wearer;

b) determination of a target value for at least one optical design parameter as a function of the mean direction of gaze, $DR_m$, determined in step a);

c) calculation of the optical system of the progressive lens for the wearer by an optical optimization procedure based on target values, where the prescription data are target values of the said calculation and where the target value of the (or of each) optical design parameter as a function of the mean direction of gaze determined in step b) is a supplementary target value of the said calculation of the optical system.

According to several embodiments which can be combined according to the technically achievable embodiments:

the mean direction of gaze, $DR_m$, is determined for a plurality of gaze directions of the wearer in a reference frame, $R_{CRO}$, tied to the head of the said wearer;

the optical design parameter of step b) is a personalized progression length chosen from among a personalized total progression length and a personalized partial progression length;

the optical design parameter of step b) is a personalized total progression length and where the target value of personalized total progression length is defined by the difference between the fitting cross and a point corresponding to the projection of the mean direction of gaze, $DR_m$, in the plane of the lens; alternatively, the optical design parameter of step b) is a personalized total progression length and where the target value of the personalized total progression length is defined by the difference between the fitting cross and a point corresponding to the result of a transfer function having as variable the point corresponding to the projection of the mean direction of gaze, $DR_m$, in the plane of the lens;

an additional target value defined as a value of a personalized partial progression length is introduced into step c) of calculation of the optical system of the progressive lens for the wearer;

the personalized partial progression length is defined by the difference between the fitting cross and a point corresponding to 85% of the prescribed addition;

the value of personalized partial progression length is the result of a transfer function having as variable a visual behaviour parameter of the individual;

providing the mean direction of gaze, $DR_m$, originates from the result of a procedure comprising the following steps:

a step of requesting the individual so that he performs a visual test in the course of which he observes at least one target position, a step of measuring at least one datum representative of at least one direction of gaze (DR) of the individual in the course of the said visual test, a step of determining a mean direction of gaze ($DR_m$), as a function of the said at least one measured representative datum, a step of positioning, with respect to the said mean direction of gaze ($DR_m$), at least one measured target position which is determined, in a reference frame ($R_{cro}$) tied to the head of the individual, as a function of the said datum representative of the said direction of gaze (DR) of the individual measured in the course of the visual test;

providing the mean direction of gaze, $DR_m$, originates from the result of a procedure comprising the following steps:

a step of requesting the individual so that he performs a visual test in the course of which he observes at least one target position of an object, a step of measuring at least one datum representative of at least one direction of gaze (DR) of the individual in the course of the said visual test, where the said direction of gaze (DR) is an observation direction which corresponds to a straight line linking a centre of rotation of an eye of the individual to a point of the object, a step of determining a mean direction of gaze ($DR_m$), as a function of the said at least one measured representative datum, a step of positioning, with respect to the said mean direction of gaze ($DR_m$), at least one measured target position which is determined, in a reference frame ($R_{cro}$) tied to the head of the individual, as a function of the said datum representative of the said direction of gaze (DR) of the individual, corresponding to the observation direction, measured in the course of the visual test;

in the procedure for providing the mean direction of gaze, $DR_m$, hereinabove:

the individual successively observes various target positions, for example of the object, the said directions of gaze (DR) of the individual are determined in the course of the visual test in the said reference frame ($R_{cro}$) tied to the head of the individual, the coordinates of the said target positions are determined in the said reference frame ($R_{cro}$) tied to the head of the individual, and the said mean direction of gaze ($DR_m$) is determined as being a straight line linking a centre of rotation of the left eye ($CRO_G$) or right eye ($CRO_D$) of the individual, or a barycentre ($CRO_c$) of the said centres of rotation, to a target position in the reference frame ($R_{cro}$) tied to the head of the individual;

in the procedure for providing the mean direction of gaze, $DR_m$, hereinabove:

the individual successively observes various target positions, for example of the object, the said directions of gaze (DR) of the individual are determined in the course of the visual test in a reference frame ($R_{cro}$) tied to the head of the individual, the coordinates of the said target positions are determined in the said reference frame ($R_{cro}$) tied to the head of the individual, a barycentre (NVB) of the said target positions in the reference frame ($R_{cro}$) tied to the head of the individual is determined on the basis of the said coordinates, and the said mean direction of gaze ($DR_m$) is determined as a straight line linking a centre of rotation of a left eye ($CRO_G$) or right eye ($CRO_D$) of the individual, or a barycentre ($CRO_c$) of the said centres of rotation, to the said barycentre (NVB) of the target positions in the reference frame ($R_{cro}$) tied to the head of the individual;

the visual behaviour parameter of the individual is provided in the course of the procedure for providing the mean direction of gaze, $DR_m$, in the course of which the visual behaviour parameter of the individual is furthermore determined according to the following steps:

positioning, with respect to the said mean direction of gaze ($DR_m$), of theoretical target positions whose relative dispositions with respect to one another are identical to the relative dispositions of the said target positions;

optionally, positioning of the said theoretical target positions so that the barycentre of the said theoretical target positions is situated on the reference direction of gaze ($DR_m$);

during the visual test, the target positions are disposed on a display surface, and, during the positioning step, a dummy display surface oriented, with respect to the said reference direction of gaze ($DR_m$), according to a mean orientation of the said display surface is determined during the visual test and the said measured target positions are determined as the intersections of the said directions of gaze (DR) of the individual in the course of the visual test and of the said dummy display surface;

differences ($\Delta v$) are determined between the said theoretical target positions and the said measured target positions according to a favoured direction of the said dummy surface and the visual behaviour parameter of the individual is deduced therefrom;

according to a complementary embodiment, the deduction of the visual behaviour parameter is performed as a function of a statistical processing of the differences ($\Delta v$) between the theoretical target positions and the measured target positions;

the calculation of the optical system of the progressive lens for the wearer by an optical optimization procedure based on target values is implemented in accordance with the teachings of patent document WO 2015/074777 A1, by substituting the optical design parameters of this document with those of the present invention.

Within the framework of the present patent application, the term "wearer" or "individual" is used interchangeably to designate the person for whom the progressive lens which is the subject of the method for determining an optical system or of the method for manufacturing a progressive lens of the present patent application is intended.

A total progression length (LPT) is defined by the vertical distance, expressed in particular in mm in the plane of the lens, between the fitting cross and the point of intersection of the direction of gaze corresponding to the near vision direction of gaze with the plane of the lens. It should be noted that a progression length can also be expressed in the form of an angular difference, in degrees, when the optical properties of a lens are considered in a reference frame ($\alpha$, $\beta$) and that this angular difference can be transformed in a known manner into a distance expressed in mm. Hereinafter in the present document, a progression length will be considered in the form of a vertical distance, expressed in mm in the plane of the lens.

The near vision direction of gaze is the direction of gaze in ($\alpha$, $\beta$), along the meridian of the lens, via which the wearer perceives a power equivalent to the far vision power increased by the prescribed addition, $ADD_p$.

In a manner known to a person skilled in the art, a reference frame ($\alpha$, $\beta$) is a reference frame making it possible to represent the optical characteristics of a lens; the definition of such a reference frame and of the expression of the optical properties in such a reference frame emerges for example from patent document WO 2015/074777 A1.

A total reference progression length ($LPT_{ref}$) is defined as the value of total progression length of a reference progressive lens. This reference progressive lens is defined at least by a fitting cross and for a given wearer having prescription data, including an addition prescribed by standard and known procedures, without implementing a step of personalizing design parameters. Consequently, the value of LPT is unique for all wearers having one and the same prescription.

A partial progression length ($LP_{x\%}$) is defined by the vertical distance, in mm in the plane of the lens, between the fitting cross and the point of intersection of the direction of gaze corresponding to the vision direction of gaze at X % of the prescribed addition with the plane of the lens.

The vision direction of gaze at X % of the prescribed addition is the direction of gaze in (α, β), along the meridian of the lens, via which the wearer perceives a power equivalent to the far vision power increased by X % times the prescribed addition ((X/100)×$ADD_p$).

According to one embodiment, a value of X lying between 15 and 90 is chosen.

According to one embodiment, a value of X equal to 85 is chosen, that is to say that the partial progression length is considered where the wearer perceives a power equivalent to the far vision power increased by 85% of the prescribed addition, which is denoted $LP_{85\%}$.

A vertical distance is defined corresponding to the difference between the fitting cross and a point corresponding to the projection of the mean direction of gaze, $DR_m$, in the plane of the lens, which distance is referred to as $LPT(DR_m)$, for "total progression length with projection of the mean direction of gaze $DR_m$". An exemplary procedure for determining a point corresponding to the projection of the mean direction of gaze, $DR_m$, in the plane of the lens is described herein below within the framework of the description of FIGS. 1 to 8.

The "plane of the lens" is defined as the tangent plane to the front face of the lens at the level of the reference point of the prism, denoted PRP. In this plane, the various points have coordinates x,y expressed in mm. For each position x,y of this plane the front face of the lens is specified by a value z, also in mm. The concept of "reference point of the prism", PRP, is usual and defined by the norms known in the field of ophthalmic optics.

The present invention also envisages a method for manufacturing a progressive lens by machining of a semi-finished lens according to the results of the calculation of the optical system of the progressive lens for the wearer of any one of the preceding claims.

The present invention also envisages a computer program product comprising a plurality of recorded sequences accessible to a processor and which, when it is executed by the processor implements the steps of the method according to the embodiments hereinabove.

The present invention also envisages a medium readable by a computer comprising the instructions for the computer program product hereinabove.

The description which follows with regard to the appended drawings and embodiments hereinbelow, given by way of nonlimiting examples, will clearly elucidate the gist of the invention and how it can be embodied.

Figure 1:
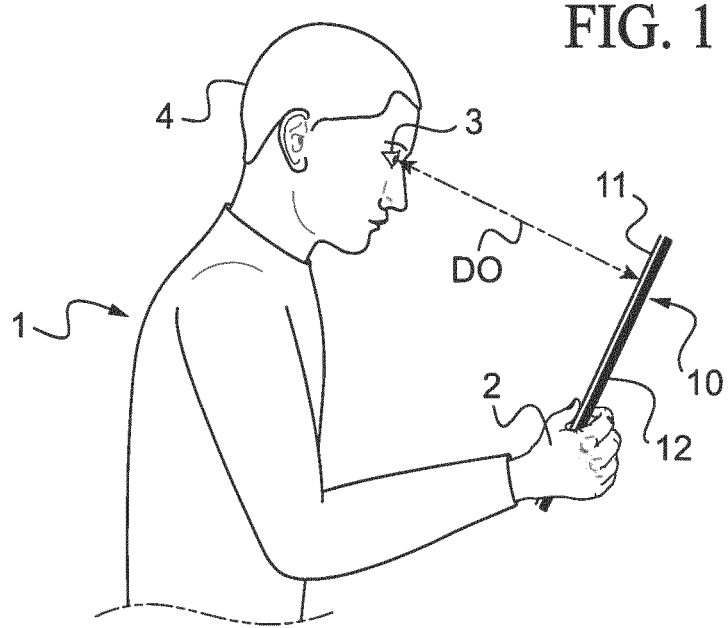
FIG. 1 is a schematic view of an individual holding in his hands a test device in accordance with the invention.

In the examples which will follow of the method according to the present invention for determining an optical system of a progressive lens:

the progressive lens is defined at least by a fitting cross and is personalized for a given wearer having prescription data, including a prescribed addition;

the method is implemented by computing means and comprises the following consecutive steps:

a) providing a mean direction of gaze, $DR_m$, determined for the wearer in a reference frame, $R_{CRO}$, tied to the head of the said wearer;

b) determination of a target value for at least one optical design parameter as a function of the mean direction of gaze, $DR_m$, determined in step a), where the optical design parameter of step b) is a personalized total progression length;

c) calculation of the optical system of the progressive lens for the wearer by an optical optimization procedure based on target values, where the prescription data are target values of the said calculation and where the target value of the personalized total progression length as a function of the mean direction of gaze determined in step b) is a supplementary target value of the said calculation of the optical system.

According to a first embodiment, the target value of personalized total progression length, hereinafter dubbed $LPT_{perso}$, is equal to the total progression length with projection of the mean direction of gaze $DR_m$, $LPT(DR_m)$. This embodiment is dubbed "Identity".

According to another embodiment, the target value of personalized total progression length, LPTperso, is equal to the difference between the fitting cross and a point corresponding to the projection of an estimated direction of gaze DRe deduced from a transfer function having as variable the mean direction of gaze, DRm, in the plane of the lens.

The transfer function is defined by the formulae:

Downward estimated direction of gaze=1.55×Downward mean direction of gaze−9.37.

According to another embodiment, the target value of personalized total progression length, $LPT_{perso}$, is equal to the difference between the fitting cross and a point corresponding to the result of a transfer function having as variable the point corresponding to the projection of the mean direction of gaze, $DR_m$, in the plane of the lens.

According to a complementary embodiment, the total progression length with projection of the mean direction of gaze $DR_m$, $LPT(DR_m)$, is an input parameter of the said transfer function.

According to a complementary embodiment, we define a minimum value of personalized total progression length, $LPT_{min}$, a maximum value of personalized total progression length, $LPT_{max}$, and a function between these two bounds with $LPT(DR_m)$, as variable, and where the result of the transfer function is equal to the result of this function for the value LPT(DR$_m$) measured for a given wearer.

According to a complementary embodiment, the transfer function dubbed "FT1" is defined as follows:

LPT$_{min}$=14 mm

LPT$_{max}$=18 mm

If LPT(DR$_m$) measured for a given wearer is less than or equal to 10 mm, then LPT$_{perso}$ equal to LPT$_{min}$;

If LPT(DR$_m$) measured for a given wearer is greater than or equal to 19 mm, then LPT$_{perso}$ equal to LPT$_{max}$;

If LPT(DR$_m$) measured for a given wearer is greater than or equal to 10 mm and less than or equal to 19 mm, then LPT$_{perso}$=16+1.55×Arctangent (LPT(DR$_m$)−14.5).

According to another embodiment, an additional target value defined as a value of a personalized partial progression length is introduced into step c) of calculation of the optical system of the progressive lens for the wearer.

According to a complementary embodiment, the personalized partial progression length is defined by the difference between the fitting cross and a point corresponding to 85% of the prescribed addition.

According to a complementary embodiment, the value of personalized partial progression length is the result of a transfer function having as variable a visual behaviour parameter of the individual.

According to a complementary embodiment, the visual behaviour parameter of the individual is defined as a function of a statistical processing of the differences (Δv) between the theoretical target positions and the target positions measured in the course of a visual test.

According to a complementary embodiment, the visual behaviour parameter of the individual is defined in such a way that its value lies between 0 and 1.

According to an embodiment, providing the mean direction of gaze, DR$_m$, originates from the result of a procedure comprising the following steps:

a step of requesting the individual 1 so that he performs a visual test in the course of which he observes at least one target position 30 of an object, a step of measuring at least one datum representative of at least one direction of gaze (DR) of the individual 1 in the course of the said visual test, where the said direction of gaze is an observation direction which corresponds to a straight line linking a centre of rotation of an eye of the individual 1 to a point of the object, a step of determining a mean direction of gaze (DR$_m$), as a function of the said at least one measured representative datum, a step of positioning, with respect to the said mean direction of gaze (DR$_m$), at least one measured target position 50 which is determined, in a reference frame (R$_{cro}$) tied to the head 4 of the individual 1, as a function of the said datum representative of the said direction of gaze (DR) of the individual 1, corresponding to the observation direction, measured in the course of the visual test.

In the frame of the present invention, a target position of an object or a point of an object is a position or a point of an object to be seen by the wearer, as for an example it is a characteristic position or point of said object; according to an embodiment, the object is a digital tablet comprising a screen; according to an embodiment, a point of the digital tablet is chosen within the list consisting of an edge of the screen of said tablet, the barycentre of the screen of said tablet, a camera which is part of said tablet; according to a preferred embodiment, the point of the digital tablet is the barycentre of the screen of said tablet.

In said embodiment, observing a target position of an object and defining an observation direction which corresponds to a straight line linking a centre of rotation to a point of the object may be advantageous; according to an embodiment, one uses a test device 10 comprising an active display 11 which displays targets 30 at a plurality of target positions; one can for example use a plurality of targets and choose a pattern of targets which barycentre is the same than the barycentre of the object; one can also use a plurality of targets and choose a pattern of targets which barycentre is not the same than the barycentre of the object; according to an example of preceding embodiments, targets can be present in only a part of the active display, for example on the top part of said display; this allows determining how the individual posture evolves when implementing the visual test so as to determine the mean direction of gaze.

An exemplary procedure for determining a visual behaviour parameter of the individual is described hereinbelow within the framework of the description of FIGS. 6 to 10.

According to a complementary embodiment, the personalized partial progression length, dubbed LP$_{85perso}$, is defined by the difference between the fitting cross and a point corresponding to 85% of the prescribed addition, this value of personalized partial progression length is the result of a transfer function, dubbed "FT2", having as variable a visual behaviour parameter of the individual, dubbed "RATIO" defined in such a way that its value lies between 0 and 1.

According to an embodiment, RATIO can be calculated thanks to a statistical analysis of the angular dispersion of the object.

According to a complementary embodiment, the transfer function FT2 is defined as follows:

If RATIO measured for a given wearer is greater than or equal to 0.8, then: LP$_{85perso}$=LP$_{85/LPTperso}$;

If RATIO measured for a given wearer is less than or equal to 0.4, then: LP$_{85perso}$=LP$_{85/LPTperso}$−(−3.5×RATIO+2);

If RATIO measured for a given wearer is greater than 0.4 and less than 0.8, then: LP$_{85perso}$=LP$_{85/LPTperso}$−(−1.5×RATIO+1.2);

Furthermore the value LP$_{85perso}$ is at least equal to LP$_{85min}$.

LP$_{85/LPTperso}$ is the value LP$_{X\%}$, for X=85, of the personalized lens when the latter has been optimized in step c) using the design parameter LPT=LPTperso;

LP$_{85min}$ is the value LP$_{X\%}$, for X=85, of the personalized lens when the latter has been optimized in step c) using the design parameter LPT=LPTmin=14 mm.

It goes without saying that other transfer functions can be envisaged than those detailed hereinabove.

By way of example, an alternative to the transfer function FT2, hereinafter dubbed FT2', is defined as follows:

If RATIO measured for a given wearer is greater than 0.8, then: LP$_{85perso}$=LP$_{85/LPTperso}$;

If RATIO measured for a given wearer is less than or equal to 0.8, then: LP$_{85perso}$=LP$_{85/LPTperso}$+(1−2×RATIO);

Furthermore the value LP$_{85perso}$ is at least equal to LP$_{85min}$.

By way of another example, an alternative to the transfer function FT2, hereinafter dubbed FT2", is defined as follows:

If RATIO measured for a given wearer is greater than or equal to 0.8, then: LP$_{85perso}$=LP$_{85ref}$;

If RATIO measured for a given wearer is less than or equal to 0.4, then: $LP_{85perso} = LP_{85ref} - (-3.5 \times RATIO + 2)$;

If RATIO measured for a given wearer is greater than 0.4 and less than 0.8, then: $LP_{85perso} = LP_{85ref} - (-1.5 \times RATIO + 1.2)$.

In the preamble of the description of FIGS. 1 to 10, it will be noted that identical or similar elements of the various embodiments represented in the various figures will be referenced by the same reference signs and will not be described each time.

It will also be noted that in the disclosure which will follow, the terms "top" (or "upper") and "bottom" (or "lower") will be used in relation to the individual using the test device, top designating the side turned towards the head of the individual and bottom designating the side turned towards the feet of the individual.

Likewise, the term "front" will designate the side turned towards the individual, the term "rear" designating the side opposite to the front side.

In FIG. 1 has been represented an individual 1 whose visual behaviour it is desired to test.

For this purpose, the individual 1 holds in his hands 2 a test device 10 intended to determine this visual behaviour under given conditions.

More particularly here, it is desired to use the test device 10 to analyse in a general manner the near vision of the individual 1, and in particular the visual behaviour that he adopts when he is in a reading situation.

It will be considered that near vision corresponds to an observation distance DO (see FIG. 1) between the eye 3 of the individual 1 and the test device 10 of less than 70 centimetres (cm).

In other embodiments, intermediate vision (DO lying between 40 cm and 4 metres) or far vision (DO greater than 4 m) can be tested by virtue of the test device.

The test device 10 comprises (see FIGS. 1 and 2):
- an active display 11 which displays a visually predominant target 20 at a plurality of target positions 30 aligned according to at least two substantially parallel lines or columns, and
- a control unit (not represented) for the display 11, programmed so that the target positions 30 define, in the course of time, a protocol for visual tracking so as to reproduce the displacement of the gaze of the individual while reading.

The display 11 of the test device can display, at each instant of the visual test, one single target or else several targets simultaneously. In both cases, the visually predominant target is that which is suitable for catching the gaze of the individual and which the individual will follow in the course of the visual test.

When several targets are displayed by the display 11, the visually predominant target can be, for example, a more luminous or more contrasted target, of different colour or shape (round, square, star, . . . ), or of smaller or larger size than the others, or else a target which blinks whereas the others do not blink. The various targets displayed by the display can also comprise a set of indicators or else form a grid of grey dots.

In the embodiments where the display 11 displays only a single target 20 (case of FIG. 2), the latter can take a plurality of target positions 30 on the display 11. These target positions 30 are "variable" in the sense that the target 20 moves sequentially from one target position 30 to another in the course of the visual test. It will nonetheless be noted that the sequence of target positions 30 taken successively by the target 20 in these embodiments can comprise two identical target positions 30. Stated otherwise, it is possible that in the course of the visual test the target 20 reverts to a target position 30 already taken previously.

In the embodiments where the display displays several targets, one of which is visually predominant, the display positions of the targets can be variable in the course of time, but in any event, the visually predominant target is the one which moves according to a sequence of target positions in such a way as to impose on the individual 1 a succession of particular directions of gaze.

In the present description, "visual tracking protocol" will be intended to mean the display sequence of the visually predominant target 20 in the course of the visual test carried out by the individual 1.

Stated otherwise, this visual tracking protocol corresponds to the succession, over time, of the target positions 30 taken by the visually predominant target 20. By virtue of this, a protocol is imposed on the individual 1 who gazes successively in a plurality of desired particular directions which are each associated with a particular target position 30 taken by the target 20. In this manner, if the target positions 30 of this target 20 are known, it is then possible, under certain conditions, to get back to the information relating to the direction of gaze of the individual 1 during the visual test.

In the subsequent description, "direction of gaze" of the individual 1 associated with a target position 30 of the target 20, will be intended to mean the direction of the straight line passing through:
- one of the centres of rotation of the right eye or of the left eye of the individual 1, or a barycentre of these centres of rotation; and
- the said target position 30 when the individual 1 observes the target 20 taking this target position 30.

Figures 2, 5:
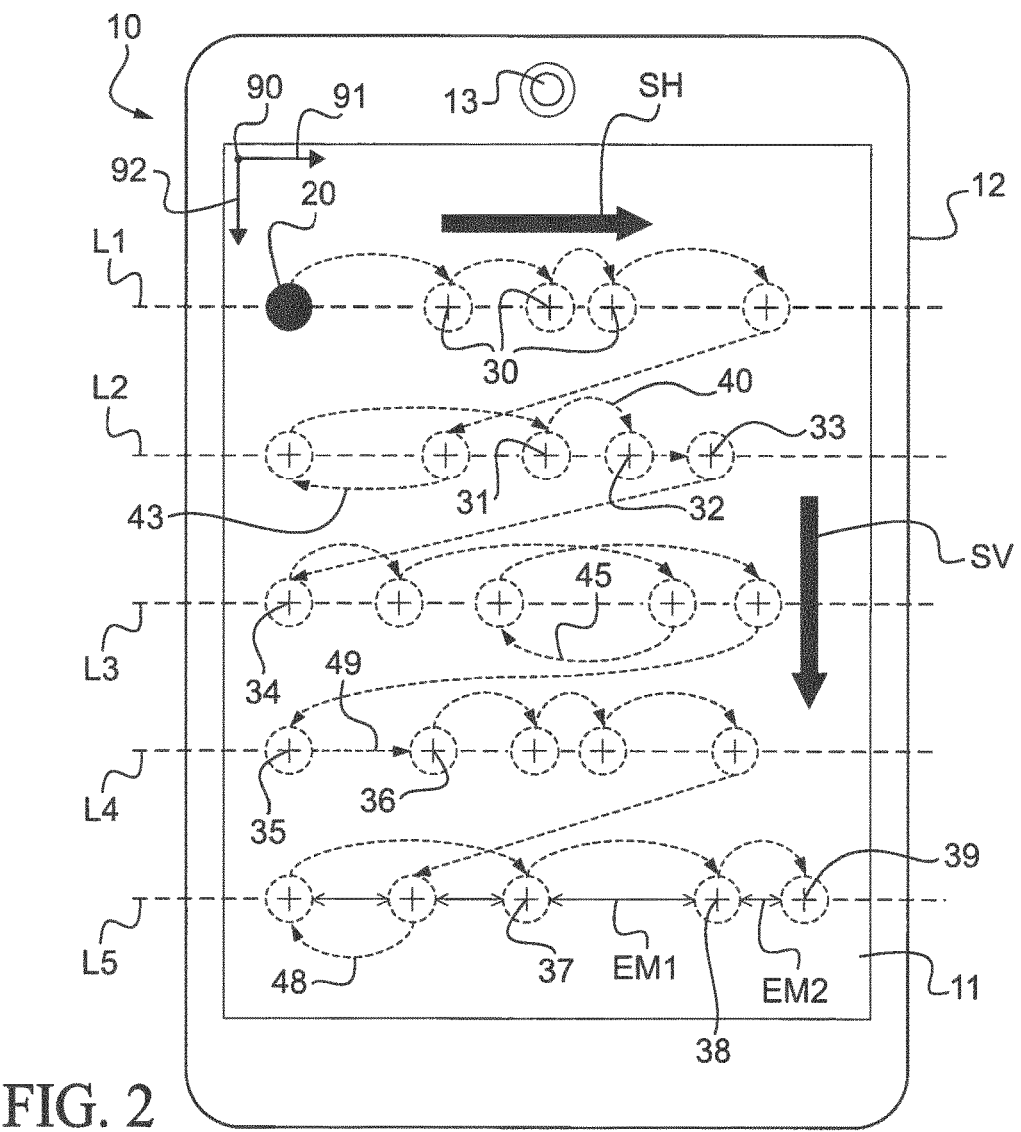
FIG. 2 is an end-on view of the test device of FIG. 1 on which is displayed a visual target moving according to a visual tracking protocol.
FIG. 5 represents a display of the test device of FIG. 1 with a displayed target and a reference frame tied to the head of the individual looking at the target in a final position of the protocol.

As illustrated in FIG. 2, here the test device 10 takes the form of a digital tablet. This digital tablet comprises a screen which constitutes the display 11 of the test device 10. It also comprises a housing 12 surrounding the screen. The control unit of the test device 10 corresponds, for its part, to the display controller for the tablet's screen 11 which is accommodated inside the housing 12.

The test device 10 also comprises an image capture apparatus 13 which is driven by the control unit in a manner synchronous with the display 11 so as to trigger captures of images of the head 4 of the individual 1 observing the target 20 displayed by the display 11, each captured image corresponding to a predetermined target position 30.

Preferably, here the frontal camera 13 integrated into the tablet 10 is used as image capture apparatus of the test device. This frontal camera 13 exhibits the advantage of always facing and of sighting the individual 1 during the visual test performed by the individual 1.

In other embodiments, provision may be made to use an image capture apparatus which is separate and distinct from the display.

Here the target 20 comprises a luminous disc which is displayed on the screen of the tablet, the size of the target being sufficient for it to be visible by the individual 1 under the conditions of the visual test. Here, in reading conditions and in near vision (DO<70 cm), the target 20 has a characteristic size (e.g. diameter) of greater than 5 millimetres.

In an advantageous manner, the characteristic size of the target 20 is determined in such a way that it can be seen with an acuity of greater than 0.1 tenths at 70 cm.

As a variant, the target can comprise a geometric pattern, regular or otherwise. This preferably entails an arbitrary pattern, with the exclusion of a sign used by an arbitrary writing system comprehensible to the individual. In particular, the visually predominant target is divested of meaning for the individual. For example, the target is not a word which is intelligible to the individual.

The visual tracking protocol which is implemented by the test device 10 and which is intended here to simulate the reading of a text by the individual 1 will now be described with reference to FIG. 2.

In an advantageous manner, the display of the target according to the visual tracking protocol implemented by the test device 10 constitutes a visual stimulus for the individual 1, intended to make him move his eyes 3 by tracking this target 20 according to the same scheme as that which the individual 1 would adopt if he were actually reading a text.

Stated otherwise, the display of the visually predominant target 20 on the display 11 is controlled in such a way that, when the individual 1 follows with his gaze the target 20 from one target position 30 to another, the direction of the gaze of the individual 1 exhibits successive directions of gaze which are entirely similar to the directions of gaze that this individual 1 would have when reading a text.

The sequence of the target positions 30 taken successively by the visually predominant target 20 is preferably predetermined as a function of a reference text, and/or of a reading model, corresponding to the characteristics and/or to the reading/writing preferences of the individual.

For example, the sequence can be predetermined previously with another device, in the course of a calibration operation during which the individual is asked to choose a reference text from among a plurality of available actual texts and to read it aloud. The reading speed can then serve as parameter for the determination of the display positions of the target.

The sequence can also be predetermined as a function of the individual's age or as a function of a reading level declared by the individual, subsequent to a questionnaire filled in by the individual.

It is also possible to envisage doing a training run with a mean speed, asking the individual if this mean speed was too fast or not fast enough and adjusting the speed as a function of his response.

It will be observed firstly that the reading of a text by an individual is done naturally according to a reading scheme comprising three distinct operations: fixations, saccades and reverse saccades.

During fixations, the individual deciphers the word that he is in the process of reading, that is to say the word on which the individual's gaze is fixed.

During saccades, corresponding to the displacement phases, that is to say to passing from the reading of one word to the following word, the individual's eyes move rapidly so as to pass from one fixation to another.

These saccades are related to the visual span, that is to say to the number of characters (letters, symbols, ideograms, etc.) which are decipherable for a given fixation. They allow the reader to decipher all the characters of a text.

The saccades generally take place in the direction of reading of the text. Nonetheless, the eyes also perform very fast "reverse saccades" in the direction opposite to the direction of reading so as to pass from one fixation to another. This movement is induced by an error of the oculomotor muscles or by poor reading and understanding of the text.

One of the advantages of the test device 10 is to propose visual tracking protocols which come as close as possible to the individual's reading schemes.

The test device 10 therefore makes it possible to simply simulate the reading of a text and to place the individual in a situation where he will adopt a natural posture close to that which he would adopt for reading in near vision.

A determination of the visual behaviour of the individual under these conditions is therefore rendered more precise and the optical design of an ophthalmic lens intended for the individual can be improved so that the design of the ophthalmic lens meets the individual's visual needs.

Preferably, the target positions 30 of the target 20 are aligned according to at least two substantially parallel lines. More precisely, in the exemplary embodiment shown in the figures, the control unit for the display 11 is programmed so that the successive target positions 30 of the target 20 are aligned with five lines L1, L2, L3, L4, L5 (see FIG. 2).

Alternatively, the target positions of the target can be aligned according to at least or two columns.

Generally, the target positions 30 of the target 20 can define parallel lines of arbitrary direction, in particular substantially horizontal or vertical for the individual 1.

Preferably again, each line, or alternatively each column, comprises at least three aligned positions of the said target (case of the positions 35, 36, 37, 38, 39 for the line L5 of FIG. 2).

In order that the visual tracking protocol is most representative of a reading by the wearer, provision is advantageously made for the visual tracking protocol to describe a reading trajectory which accords with that defined by a given writing system, so as to reproduce the displacement of the gaze of the individual while reading in accordance with the writing system.

The reading trajectory can be defined here as the path, at the level of the display 11, scanned by the direction of gaze of the individual 1 when he gazes at the sequence of target positions 30 taken by the visually predominant target 20.

The reading scheme adopted by an individual is related not only to the nature or to the specific properties of the text, but also to the specific features of each type of writing.

It will be noted moreover that the various types of writing can be classified in a functional manner (alphabetic, syllabic or logographic writing) and a directional manner (horizontal and vertical direction of writing and/or reading).

Provision is therefore made in the test device for the control unit to store a favoured vertical SV and horizontal SH direction of travel (see FIG. 2) of the visual tracking protocol.

This favoured vertical and horizontal direction of travel is previously determined as a function of the characteristics of the individual, and in particular his ability to read a text according to a given writing system.

For example, when the test device is used by a French person who reads from right to left and from top to bottom, the horizontal direction of travel stored by the control unit is a direction of travel going from the left of the screen 11 to the right of the screen 11, and the vertical direction of travel stored by the control unit is a direction of travel going from the top of the screen 11 to the bottom of the screen 11.

Hence, in a preferred embodiment, the substantially parallel lines L1, L2, L3, L4, L5 along which the target positions 30 of the target 20 are aligned extend substantially horizontally, the direction of travel of the visual tracking protocol being identical for all the lines taken successively from the topmost to the bottommost, from left to right (or from right to left for right-to-left writing such as Arabic or Hebrew).

In the same manner, when the test device is used by a Mongolian, who reads from top to bottom and from right to left, the vertical direction of travel stored by the control unit is a direction of travel going from the top of the screen to the bottom of the screen, and the horizontal direction of travel stored by the control unit is a direction of travel going from the right of the screen to the left of the screen.

Hence, in an embodiment suitable for this writing system, the substantially parallel lines along which the predetermined positions of the target are aligned extend substantially vertically, the direction of travel of the visual tracking protocol being identical, from top to bottom or from bottom to top, for all the lines taken successively from right to left.

In an advantageous manner, the control unit of the test device 10 is programmed to allow the selection of the visual tracking protocol from among a plurality of visual tracking protocols recorded in a local or remote database, in which a direction of travel is recorded in association with the visual tracking protocol to which it corresponds.

Thus, the individual as a function of his own reading and/or writing characteristics can choose the visual protocol which corresponds to him, so that he is under natural reading-like conditions whilst carrying out the visual test. It is then certain that his reading mechanisms and strategies are put in place so as to recover the posture which is most representative of the use of his near vision.

In order to reproduce the reading scheme such as described above, with fixations, saccades and reverse saccades, provision is made for the control unit of the display 11 to display the target 20 according to a preferential visual tracking protocol.

Hence, provision is made for the control unit to require, in each target position 30 of the visual tracking protocol, that the target 20 be displayed for a predetermined duration. This is intended to mean that the target 20 is kept displayed fixedly on the screen in such a way that the individual 1 is forced to fix his gaze on the target 20, thus corresponding to a fixation on the target position 30 in the reading trajectory of the individual 1.

In an advantageous manner, the target 20 is fixed for the predetermined duration, that is to say that the target position 30 of the target 20 for this predetermined duration does not change, before passage to the following target position of the reading trajectory.

Preferably, this predetermined duration lies between 50 milliseconds and 1 second, thus corresponding typically to standard fixation times.

The predetermined duration can also vary in the course of the reading trajectory, this accounting for the fact that the fixation of the gaze of the individual 1 on a word during actual reading may depend on the word (size, length) and on the level of understanding of this word (poorly known or unknown word, nearly indecipherable word or character, poorly spelt word, etc.).

In an advantageous manner also, provision is made for the control unit to impose a predetermined lag between the displays of the target 20 in two successive target positions (see for example the target positions 31, 32 in FIG. 2) of the visual tracking protocol.

In this manner, it is possible to simulate by virtue of the test device 10 the saccades or reverse saccades existing along the reading trajectory of the individual 1. As previously, provision may be made for the control unit to vary the predetermined lag in the course of the visual tracking protocol.

This makes it possible to allow for the fact that the reading speed of the individual 1 may vary in the course of the reading of a text.

This also makes it possible to envisage the cases where the direction of gaze of the individual 1 passes from one line to another, as is the case for example from the target position 33 to the target position 34 of FIG. 2, returning to the line requiring more time in so far as the variation of direction of gaze of the individual 1 is more significant.

It is then possible to provide two cases for the target during the predetermined lag.

In one embodiment, provision may be made for the target to be invisible during the predetermined lag. This corresponds to the case of the target positions 31 and 32 of FIG. 2 where the target 20 "jumps" (the jump being represented by the dotted arrow 40) from the position 31 to the following position 32. This embodiment makes it possible to allow for the gaze of the individual that jumps from word to word while reading a text.

In an alternative embodiment, provision may be made for the target to be visible during the predetermined lag and to move between the two corresponding successive target positions of the visual tracking protocol, from one to the other. This corresponds to the case of the target positions 35 and 36 where the target moves (the movement being represented by the dotted arrow 49), while remaining visible.

In an advantageous manner, the test device 10 is such that the control unit requires that two successive target positions 37, 38, 39 of the visual tracking protocol be separated by a distance EM1, EM2 of less than 10 centimetres. In this manner, during the visual test, the individual 1 is not requested in such a way that the variation of his direction of gaze is not too significant, which in a reading condition is generally the case.

Preferentially, provision is moreover made for the control unit to require that the distance EM1, EM2 separating two successive target positions 37, 38, 39 of the visual tracking protocol vary along the visual tracking protocol. This makes it possible to adapt the difference between the targets 20 displayed as a function of the mean span of the words for a given writing system.

In another embodiment, the control unit is programmed so that the display of the target 20 in two successive target positions of the visual tracking protocol follows the favoured direction of travel, horizontal and/or vertical, at least six times out of ten. This is illustrated in FIG. 2 in which directions of travel have been represented in the visual tracking protocol, represented by the dotted arrows 43, 45, 48, which go not from left to right like the favoured horizontal direction of travel SH, but from right to left.

It is thus possible by virtue of this to simulate the reverse saccade movements previously described while the individual 1 is reading a text. Indeed, here four times out of ten, the movement of the eyes 3 of the individual 1 following the target 20 of the gaze between two successive target positions 30 takes place in the direction opposite to the favoured direction of travel.

Just as for the saccade movements detailed above, the target 20 can pass from one target position to the following target position, in a direction of travel opposite to the favoured direction of travel, either by jumping from one position to the other (invisible target), or by moving from one to the other (visible target).

A procedure for determining at least one visual behaviour parameter of the individual 1 will now be described with reference to FIGS. 3 to 10, this procedure using the test device described hereinabove which is particularly suitable for the implementation of this procedure.

The determination procedure comprises the following steps:
- a step of requesting the individual so that he performs a visual test in the course of which he observes at least one target position,
- a step of measuring a datum representative of at least one direction of gaze of the individual in the course of the said visual test,
- a step of determining a reference direction of gaze, as a function of the said measured representative data,
- a step of positioning, with respect to the said reference direction of gaze, at least one measured target position which is determined as a function of the said datum representative of the said direction of gaze of the individual measured in the course of the visual test.

Advantageously, a step of deducing, as a function of the said at least one measured target position, the visual behaviour parameter of the individual is carried out after the positioning step.

In practice, the tablet 10, or a local or remote computer, is programmed to accomplish the above steps detailed below.

Preferably, in the requesting step of the determination procedure, the individual 1 successively observes various target positions 30.

The individual 1 is therefore requested to observe the screen 11 of the tablet 10 which displays the visually predominant target 20 according to a predetermined sequence of target positions 30 of the chosen visual tracking protocol such as described above with reference to FIG. 2.

According to a first variant embodiment, the determination procedure comprises following intermediate steps:
- the said directions of gaze of the individual are determined in the course of the visual test in a reference frame tied to the head of the individual,
- the coordinates of the said target positions are determined in the said reference frame tied to the head of the individual, and
- a barycentre of the said target positions in the reference frame tied to the head of the individual is determined, on the basis of the said coordinates, and
- the said reference direction of gaze is defined as a straight line linking a centre of rotation of a left eye or right eye of the individual, or a barycentre of the said centres of rotation, to the said barycentre of the target positions in the reference frame tied to the head of the individual.

As benchmark tied to the head 4 of the individual 1, it is for example possible to choose a benchmark termed the "primary gaze benchmark" or "reference frame CRO", in which the head 4 of the individual 1 exhibits a fixed position and orientation and with which is associated a reference frame, preferably orthonormal, having an origin and three unrelated axes.

Figure 3:
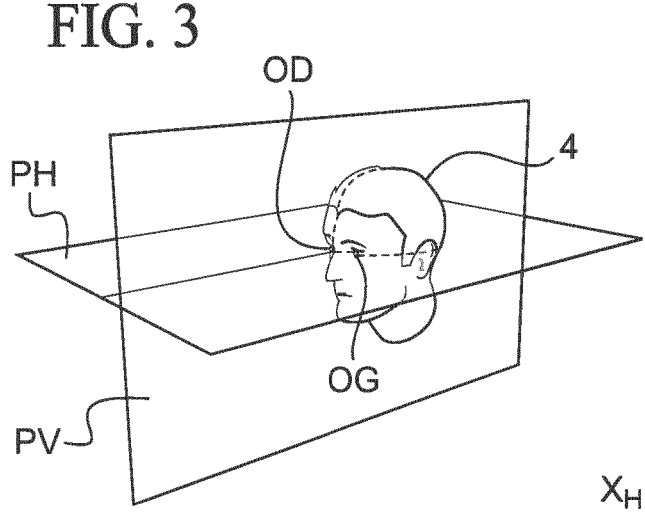
FIG. 3 is a schematic view of the head of the individual and of various planes associated with this head.
Figure 4:
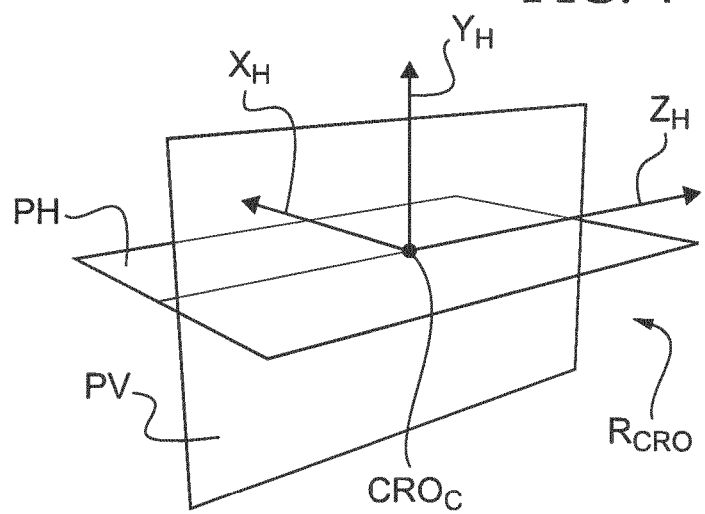
FIG. 4 represents a reference frame tied to the head of the individual.

FIGS. 3 and 4 illustrate how this reference frame CRO is constructed.

In particular, in FIG. 3 has been represented a vertical plane PV corresponding to a sagittal plane of the head 4 of the individual 1 which is the vertical plane passing through a perpendicular bisector of the two eyes, right and left, OD, OG of the individual 1.

This perpendicular bisector of the eyes OD, OG is an axis which passes in the middle of a segment which is defined by the centre of rotation of the right eye OD (hereinafter referenced CROD) and the centre of rotation of the left eye OG (hereinafter referenced CROG) and which is parallel to the Frankfurt plane of the head 4 of the individual 1.

The Frankfurt plane of the head of the individual is defined as the plane passing through the lower orbital points of the individual 1 and the portion of the individual 1, the portion being the auditory canal's highest point of the skull, which corresponds to the tragion of the ear. For the determination of the Frankfurt plane, it is considered that the individual is in an orthostatic position, in which he exerts minimum effort. This position corresponds to a natural posture, hereinafter designated "primary gaze posture".

In this natural position, the direction of gaze of the individual is then the primary direction of gaze, that is to say that he gazes straight ahead. The Frankfurt plane is then generally horizontal.

One defines moreover (see FIG. 3) a plane PH which contains the centres of rotation CROD, CROG of the eyes OD, OG of the individual 1.

In the particular example described here, this plane PH is parallel to the Frankfurt plane of the head 4 of the individual 1 and is therefore horizontal. On the basis of the primary gaze posture of the individual 1, that is to say of the knowledge of the orientation of the Frankfurt plane, and of the centres of rotation CROD, CROG of the eyes OD, OG of the individual 1, it is possible to construct the reference frame CRO tied to the head 4 of the individual 1, hereinafter referenced $R_{cro}$, by choosing:
- an origin which is one of the centres of rotation CROD, CROG of the right eye OD or of the left eye OG of the individual 1 or a barycentre of these centres of rotation CROD, CROG;
- a first axis which is parallel to a primary direction of gaze of the individual 1;
- a second axis which is horizontal and perpendicular to the first axis, and
- a third axis which is perpendicular to the first axis and to the second axis.

In the exemplary embodiments described, the origin of the reference frame $R_{cro}$ is chosen as being the point situated in the middle of the segment joining the centre of rotation CROD of the right eye OD and the centre of rotation CROG of the left eye OG of the individual 1. Stated otherwise, this origin point, designated hereinafter "cyclops CRO" and referenced $CRO_c$ corresponds to the isobarycentre of the centres of rotation CROD, CROG of the eyes OD, OG of the individual 1.

The three axes $X_h$, $Y_h$, $Z_h$, of the reference frame $R_{cro}$ are also represented in FIG. 4.

The axis $X_h$ (second axis) passes through the cyclops CRO, $CRO_c$ and is oriented here from the left centre of rotation CROG to the right centre of rotation CROD. The axis $X_h$ is horizontal here since it is contained in the horizontal plane PH parallel to the Frankfurt plane. An opposite orientation is also possible.

The axis $Z_h$ (first axis) is parallel to the primary direction of gaze when the individual 1 is in a natural position, that is to say in the primary gaze posture. In the particular case described here, the axis $Z_h$ is situated in the vertical plane PV of the head 4 of the individual 1 and is parallel to the Frankfurt plane. In other cases where the head of the individual exhibits an angle of yaw, this axis $Z_h$ might not be situated in the vertical plane. The axis $Z_h$ extends here in a direction away from the head 4 of the individual 1 (towards the rear).

The axis $Y_h$ (third axis) extends, for its part, in the vertical sagittal plane PV of the head 4 of the individual 1 and is perpendicular to the Frankfurt plane. The axis $Y_h$ is therefore indeed perpendicular to the axis $X_h$ and to the axis $Z_h$. It is oriented upwards here, so that the reference frame $R_{cro}$ is right-handed.

It will be noted that the reference frame $R_{cro}$ is tied to the head 4 of the individual 1 and that therefore this reference frame $R_{cro}$ shifts with the head 4 of the individual 1, the position and the orientation of this reference frame $R_{cro}$ changing with respect to an absolute frame or a reference frame (for example a reference frame tied to the room in which the individual performs the visual test) which would not be tied to the head 4 of the individual 1 as a function of the movements of the head 4 of the individual 1.

It will be noted that the determination of the positions of the centres of rotation CROD, CROG can be carried out according to the principle known per se and set forth for example in document FR 2914173, an equivalent of which in English is document US 2010/0128220.

During this determination of the centres of rotation CROD, CROG, the individual 1 wears, on his head 4, fastened to the head 4, a tagging system (metrological benchmark) or "clip" which comprises tagging elements (markers) detectable during an image capture of the head 4 of the individual 1.

To summarize, at least two images of the head 4 of the individual 1 are captured by means of an image capture apparatus:
  a first image when the individual gazes at the image capture apparatus while being positioned face-on, gazing straight ahead into the far distance (primary gaze posture), and
  a second image when the individual gazes at the image capture apparatus while being positioned three-quarters-on.

On the basis of a processing of the two captured images (see document FR 2914173), the positions of the centres of rotation CROD, CROG are deduced in a benchmark tied to the tagging system.

It is then possible to determine the "cyclops" centre of rotation, which is the isobarycentre of the two previously determined centres of rotation CROD, CROG.

For the determination of the primary gaze posture, the positions of the centres of rotation CROD, CROG are reused together with the first image captured face-on. Provision may also be made to compensate for the inclination of the tablet 10 during the latter determination.

In FIG. 5 has been represented the direction of gaze DR joining the cyclops CRO to the target 20, positioned here on the last target position of the visual tracking protocol, as well as the reference frame $R_{cro}$ tied to the head 4 of the individual 1 with its three main axes $X_h$, $Y_h$, $Z_h$.

Also represented in this FIG. 5 are the directions of gaze referenced respectively DRD and DRG corresponding to the directions of gaze for the right eye OD and the left eye OG of the individual 1.

Once the reference frame tied to the head 4 of the individual 1 has been chosen, here the reference frame $R_{cro}$, it is possible to determine, for each target position 30 of the target 20 observed on the screen 11 of the tablet 10, the coordinates of these target positions in this reference frame $R_{cro}$.

For this purpose, during the measuring step of the determination procedure:
  images of a part of the head 4 of the individual 1 observing each target position 30 are captured by means of the frontal camera 13, turned towards the head 4 of the individual 1, of the test device 10, each target position 30 being able to be predetermined in a reference frame tied to the frontal camera 13,
  these images are stored in association with the coordinates, expressed in this reference frame tied to the frontal camera 13, of the target position 30 observed by the individual 1, and
  the coordinates of the reference frame $R_{cro}$ tied to the head 4 of the individual 1 in the reference frame tied to the image capture apparatus 13 or the coordinates of the directions of gaze DR of the individual 1 in the reference frame $R_{cro}$ tied to the head 4 of the individual 1 are determined on the basis of the captured images and of the associated coordinates of the observed target position 30.

A reference frame tied to the frontal camera 13 may be for example the reference frame $R_{scr}$ of the screen 11 (see FIG. 5 for example) having as origin the top left corner 90 of the screen 11 and as axes the two mutually perpendicular axes 91, 92 directed along the columns and the lines of the screen 11.

Advantageously, the frontal camera 13 triggers an image capture of the head 4 of the individual 1 with a capture offset with respect to the moment at which the target 20 is displayed at the predetermined target positions 30 of the visual tracking protocol on the screen 11. This offset can be zero, or else preferably small, for example less than 200 milliseconds. This makes it possible to take into account the reaction time and displacement time of the eyes 3 of the individual 1 during a change of position 30 of the target 20 on the screen 11.

According to a variant, the frontal camera can also carry out a continuous video sequence, for example at a rate of twenty images per second, and extract from the video sequence the best image giving the best information on the visual behaviour of the individual during the display of the target at the corresponding target position.

Each image captured by the frontal camera 13 of the tablet 10 thus corresponds to a predetermined target position 30 of the visually predominant target 20, whose position 30 in the reference frame $R_{scr}$ tied to the image capture apparatus 13 is known perfectly.

To determine the coordinates of the reference frame $R_{cro}$ tied to the head 4 of the individual 1 in the reference frame tied to the image capture apparatus 13 or the coordinates of the directions of gaze DR of the individual 1 in the reference frame $R_{cro}$ tied to the head 4 of the individual 1, provision is made for means for processing images of the tablet 10, which consist for example of the processor of the tablet 10, which detects in the captured images of the head 4 of the individual 1 the markers of the clip worn by the individual 1 on his head 4.

The position and the orientation of the clip in the reference frame $R_{scr}$ tied to the frontal camera 13 are then determined for each captured image, that is to say for each target position 30 of the target 20 of the visual tracking protocol, for example by using the method described in document US 2010/0128220.

The positions of the centres of rotation CROD, CROG of the eyes of the individual 1 with respect to the clip being known, the position (spatial coordinates) and the orientation (angular coordinates) of the reference frame $R_{cro}$ tied to the head 4 of the individual 1 are also known with respect to the clip.

This is moreover illustrated in FIG. 5 where the reference frame $R_{cro}$ has been represented with its origin at the cyclops centre of rotation $CRO_c$ (isobarycentre of the centres of rotation CROD, CROG) and its axes $X_h$, $Y_h$, $Z_h$.

Thus, through a change of reference frame, it is possible to determine, for each target position 30 of the target 20 of the visual tracking protocol, the position and the orientation of the reference frame $R_{cro}$ tied to the head 4 of the individual 1 in the reference frame $R_{scr}$ tied to the frontal camera 13 of the tablet 10.

It is also possible to determine, for each target position 30 of the target 20 of the visual tracking protocol, the directions of gaze DR of the individual 1 in the benchmark $R_{cro}$ tied to the head 4 of the individual 1, these directions of gaze DR here joining the cyclops centre of rotation $CRO_c$, origin of the reference frame $R_{cro}$ tied to the head 4 of the individual 1, to the target 20.

It is finally possible to re-express, on the basis of the positions and orientations of the head 4 or of the directions of gaze DR of the individual 1, the target positions 30 of the target 20 in the reference frame $R_{cro}$ tied to the head 4 of the individual 1.

These target positions 30 in the reference frame $R_{cro}$ tied to the head 4 of the individual 1 are data representative of the measured directions of gaze DR of the individual 1 during the visual tracking protocol.

A reference direction of gaze is determined, after the measuring step, as a function of these representative data.

In certain embodiments, the reference direction of gaze corresponds to a direction of observation of the individual of a distant target (far vision) when the individual is in a natural posture.

In the preferred embodiment, the reference direction of gaze is a mean direction of gaze of the individual 1 in the course of the visual test.

Figure 6:
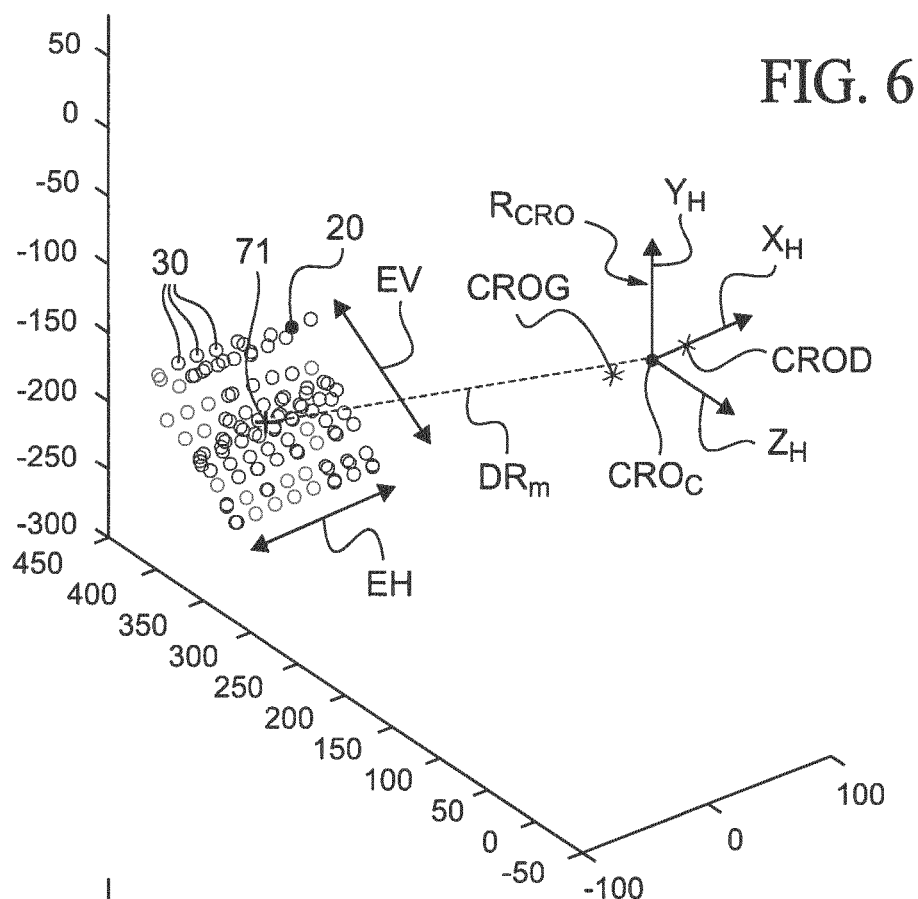
FIGS. 6 and 7 represent examples of measured positions of the target in the benchmark tied to the head of the individual in the course of the protocol.
Figure 7:
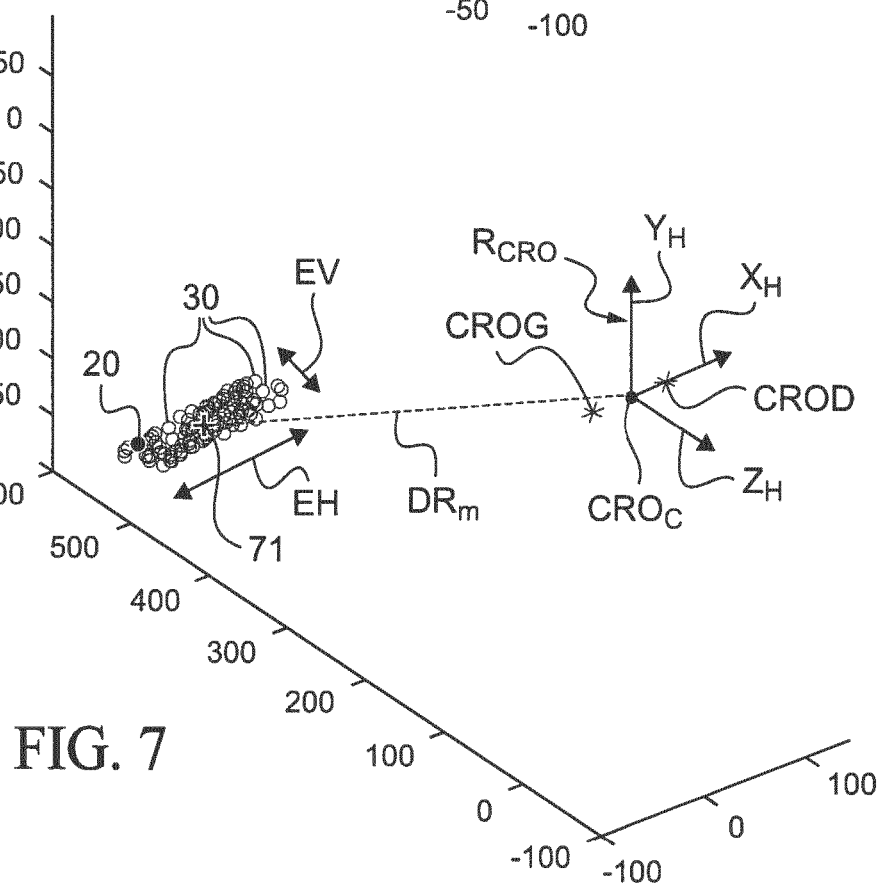

As represented in FIGS. 6 and 7, this mean direction of gaze, hereinafter referenced $DR_m$, is preferably chosen as being the straight line linking the cyclops CRO, $CRO_c$ to the barycentre 71 of the target positions 30.

As a variant, the mean direction of gaze can be defined on the basis of the right centre of rotation CROD or of the left centre of rotation CROG.

As a further variant, the mean direction of gaze is chosen here as being the straight line linking a centre of rotation of the left eye or right eye of the individual, or a barycentre of the said centres of rotation, to a target position in the reference frame tied to the head of the individual.

Having regard to the fact not only that the position and the orientation of the head 4 of the individual 1 changes in the course of the visual test protocol with respect to the reference frame $R_{scr}$ tied to the image capture apparatus 13 but also that the individual 1 modifies the position and the orientation of the tablet 10 in the course of the visual test, it is understood that the target positions 30 of the target 20 in the reference frame $R_{cro}$ tied to the head 4 of the individual 1 shed light on the visual behaviour of the individual 1, in particular on his propensity to move his eyes 3 while reading a text.

Indeed, if the individual 1 follows the visual tracking protocol while greatly modifying his direction of gaze DR, then the target positions 30 of the target 20 in the reference frame $R_{cro}$ tied to the head 4 of the individual 1 are arranged in a relatively similar way to the target positions 30 of the target 20 in the reference frame $R_{scr}$ tied to the frontal camera 13. This is the case in FIG. 6.

Conversely, if the individual 1 follows the visual tracking protocol while maintaining a quasi fixed direction of gaze DR, then the target positions 30 of the target 20 in the reference frame $R_{cro}$ tied to the head 4 of the individual 1 are grouped together. This is the case in FIG. 7.

The determination procedure moreover comprises a step of positioning, with respect to the reference direction of gaze $DR_m$, measured target positions 50 (see FIG. 8) which are determined on the basis of the directions of gaze DR of the individual 1 measured in the course of the visual test when the individual 1 follows the target positions 30 of the target 20 that are disposed on the screen 11 of the tablet 10.

Preferably, during this positioning step, a dummy display surface 111 oriented, with respect to the reference direction of gaze $DR_m$, according to a mean orientation of the screen 11 during the visual test, is also determined.

The mean orientation may for example take account of the mean angles of inclination and/or of pitch with which the individual 1 holds the tablet 10 between his hands 2 in the course of the visual test.

Figure 8:
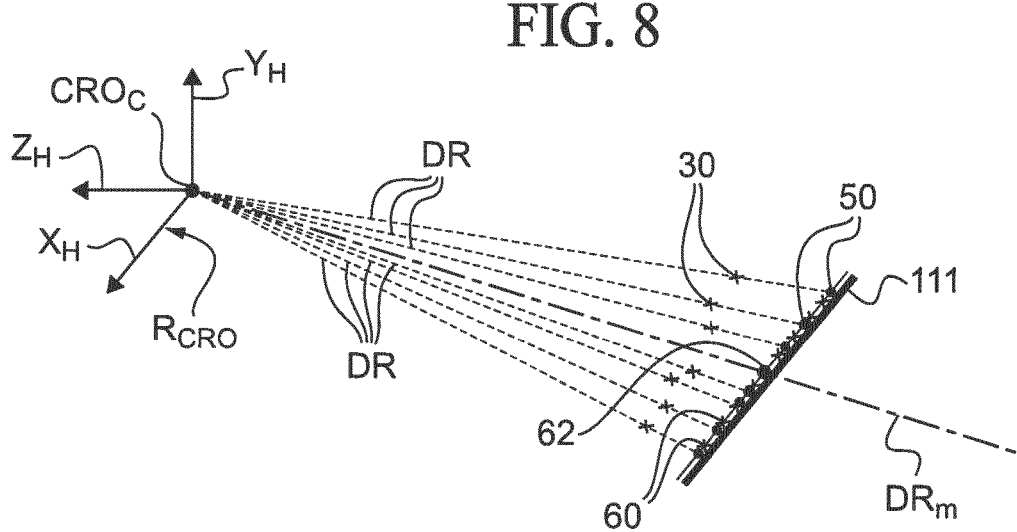
FIG. 8 is a basic diagram showing a reference direction of gaze in a benchmark tied to the head of the individual and a dummy display surface for the theoretical target positions.

As represented in FIG. 8, the measured target positions 50 (symbols "•" in FIG. 8) are also determined, during the positioning step, as the intersections of the directions of gaze DR of the individual 1 in the course of the visual test and of the dummy display surface 111.

Stated otherwise, the measured target positions 50 correspond to the projections on the dummy display surface 111 of the target positions 30, along the directions of gaze DR associated with these target positions 30.

In a preferred embodiment, the determination procedure comprises an additional positioning step.

During this additional positioning step, theoretical target positions 60 (symbols "+" in FIG. 8) whose relative dispositions with respect to one another are identical to the relative dispositions of the target positions 30 on the display surface 11 (screen) of the tablet 10, are positioned with respect to the reference direction of gaze, here the mean direction of gaze $DR_m$.

Preferably, these theoretical target positions 60 are positioned so that their barycentre 62 lies on the reference direction of gaze $DR_m$.

Figure 9:
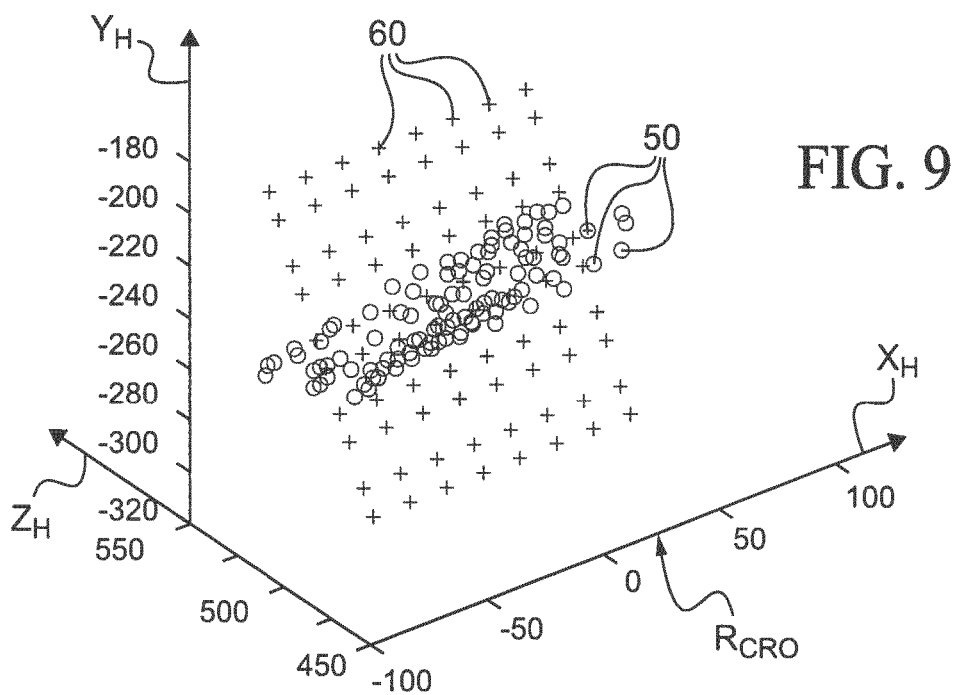
FIG. 9 represents in the benchmark tied to the head of the individual the theoretical target positions on the display surface and the target positions measured in this benchmark.

Thus, on completion of the positioning steps described above, the coordinates of the measured target positions 50, and the coordinates of the theoretical target positions 60, in the reference frame $R_{cro}$ tied to the head 4 of the individual 1, have been determined on the dummy display surface 111. This is illustrated in FIG. 9 of the drawings.

Visual behaviour parameters of the individual 1 during the visual tracking protocol can be deduced from the measured target positions 50 and from the theoretical target positions 60.

Indeed, it is already possible to determine a first visual behaviour parameter corresponding to the position (coordinates) of the barycentre (hereinafter referenced NVB for "Near-Vision Behaviour") of the target positions 30 in the reference frame $R_{cro}$ tied to the head 4 of the individual 1. This barycentre NVB sheds light in particular on the mean direction of gaze $DR_m$ of the individual 1 (cf. above) during the visual test.

Moreover, as explained above with reference to FIGS. 6 and 7, it is understood that the distribution (position and spread) of the measured target points 50 with respect to the theoretical target points 60, whose distribution on the dummy display surface 111 is fixed by that of the target positions 30 on the screen 11, sheds light on the tendency of the individual 1 to move his head 4 in relation to the display surface and/or his eyes 3 during a reading task.

Thus, in another embodiment described with reference to FIG. 10, the deducing step of the determination procedure preferably comprises a comparison of the theoretical target positions 60 and of the measured target positions 50 in the reference frame $R_{cro}$ tied to the head 4 of the individual 1.

This comparison makes it possible to deduce one or more visual behaviour parameters sought, in particular visual behaviour parameters of the individual 1 that are representative of the vertical spread EV and of the horizontal spread EH (see FIG. 6) of the target positions 30 in the reference frame $R_{cro}$ tied to the head 4 of the individual 1. The vertical spread EV, respectively the horizontal spread EH, is indeed representative of the propensity of the individual 1 to move his eyes downwards (or upwards), respectively from left to right (or from right to left), during the visual task.

In a preferred embodiment, this comparison can comprise the determination of differences between the theoretical target positions 60 and the measured target positions 50 according to a favoured direction of the dummy surface 111. This is illustrated in FIG. 10.

Figure 10:
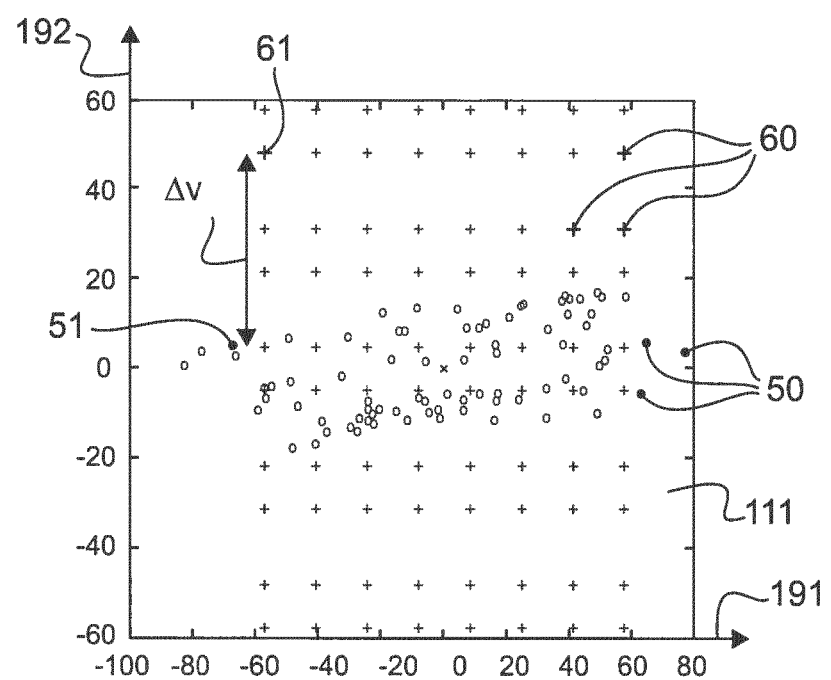
FIG. 10 is a graph illustrating the calculation of the difference between the theoretical target positions and the measured target positions.

In particular, in FIG. 10 have been represented the dummy display surface 111 endowed with axes 191, 192 oriented and normed in an identical manner to the axes 91, 92 of the screen 11 (actual display surface), the measured target positions 50 (symbols "•") as well as the corresponding theoretical target positions 60 (symbols "+").

It is possible to choose for example the vertical direction of the axis 192 as favoured direction of the dummy surface 111.

Then, for each pair formed of a measured target position 51 and of a theoretical target position 61 corresponding to the same target position 30 of the visual tracking protocol, a vertical difference is calculated, denoted here $\Delta v$, corresponding to the distance, along the vertical direction, between the measured target position 51 and the theoretical target position 61 of the said pair.

It would also be possible to choose a favoured horizontal direction (along the axis 191 of FIG. 10) and calculate horizontal rather than vertical differences.

In an advantageous manner, a statistical processing of the calculated differences is carried out to determine the visual behaviour parameter.

This statistical processing may for example comprise the following operations:
produce a mean $<\Delta v>$ per display line, of the vertical differences $\Delta v$;
perform a linear regression so as to find an approximating straight line which minimizes the difference with the measured curves.

The coefficient is in particular determined so as to lie between 0 and 1, accordingly a minimum threshold value and a maximum threshold value are determined, making it possible to norm the coefficient, for ease of use. Thus the ratio (director coefficient−minimum value/(maximum value−minimum value) is recalculated.

According to one embodiment of the present invention, providing a mean direction of gaze, $DR_m$, determined for the wearer in a reference frame, $R_{CRO}$, tied to the head of the said wearer, emerges from the procedure described hereinabove for determining at least one visual behaviour parameter of the individual, the said procedure using the test device described hereinabove.

According to one embodiment of the present invention, providing the visual behaviour parameter of the individual emerges from the procedure described hereinabove for determining at least one visual behaviour parameter of the individual, where the visual behaviour parameter of the individual is related to the differences $\Delta v$ between theoretical target positions 60 and measured target positions 50 along the favoured direction of the said dummy surface 111.

For the examples which will follow, the visual behaviour parameter of the individual, dubbed "RATIO", is defined as being the difference between the mean of the measured values $\Delta v$ and the minimum value of $\Delta v$ measured, divided by the difference between the maximum value of $\Delta v$ measured and the minimum value of $\Delta v$ measured, in such a way that the value RATIO lies between 0 and 1.

EXAMPLES

In the examples which follow, one starts from a reference lens which has the following characteristics:
prescription data:
Prescribed sphere=0 diopters
Prescribed cylinder=0 diopters
Prescribed axis=0°
Prescribed addition=2 diopters
total progression length: $LPT_{ref}$=17 mm In the examples which follow, the method for determining an optical system of a progressive lens according to the invention is implemented, starting in the calculation of the optical system of the reference progressive lens hereinabove and having the same prescription data as target values.

The parameters of such a nature as to make it possible to determine the supplementary target value(s) used in the calculation of the optical system of the progressive lens of the examples emerge from the data hereinbelow:

Example 1

$LPT(DR_m)$=16 mm,
$LPT_{perso}$ determined by Identity, therefore $LPT_{perso}$=16 mm
No taking into account of a personalized partial progression length.

Example 2

$LPT(DR_m)$=14.5 mm,
$LPT_{perso}$ determined by FT2, therefore $LPT_{perso}$=16 mm
No taking into account of a personalized partial progression length.

Example 3

$LPT(DR_m)$=14.5 mm,
$LPT_{perso}$ determined by FT2, therefore $LPT_{perso}$=16 mm
Taking into account of a personalized partial progression length and RATIO=0.9 and application of FT2;
therefore, $LP_{85perso}=LP_{85/LPTperso}$;
where $LP_{85/LPTperso}$ is the value $LP_{X\%}$, for X=85, of the personalized lens when the latter has been optimized in step c) by using the design parameter $LPT=LPT_{perso}$ Example 4

$LPT(DR_m)$=14.5 mm,
$LPT_{perso}$ determined by FT2, therefore $LPT_{perso}$=16 mm
Taking into account of a personalized partial progression length and RATIO=0.47 and application of FT2;
therefore, $LP_{85perso}=LP_{85/LPTperso}-0.5$ mm;
where $LP_{85/LPTperso}$ is the value $LP_{X\%}$, for X=85, of the personalized lens when the latter has been optimized in step c) by using the design parameter $LPT=LPT_{perso}$ Example 5

$LPT(DR_m)$=15.5 mm,
$LPT_{perso}$ determined by FT2, therefore $LPT_{perso}$=17 mm Taking into account of a personalized partial progression length and RATIO=0 and application of FT2;

therefore, $LP_{85perso} = LP_{85/LPTperso} - 2$ mm.;

where $LP_{85/LPTperso}$ is the value $LP_{X\%}$, for X=85, of the personalized lens when the latter has been optimized in step c) by using the design parameter LPT=LPTperso FIGS. 11 to 19 represent the optical properties of three progressive lenses obtained by virtue of the method of the present invention, compared with those of the reference progressive lens mentioned hereinabove.

Figure 11:
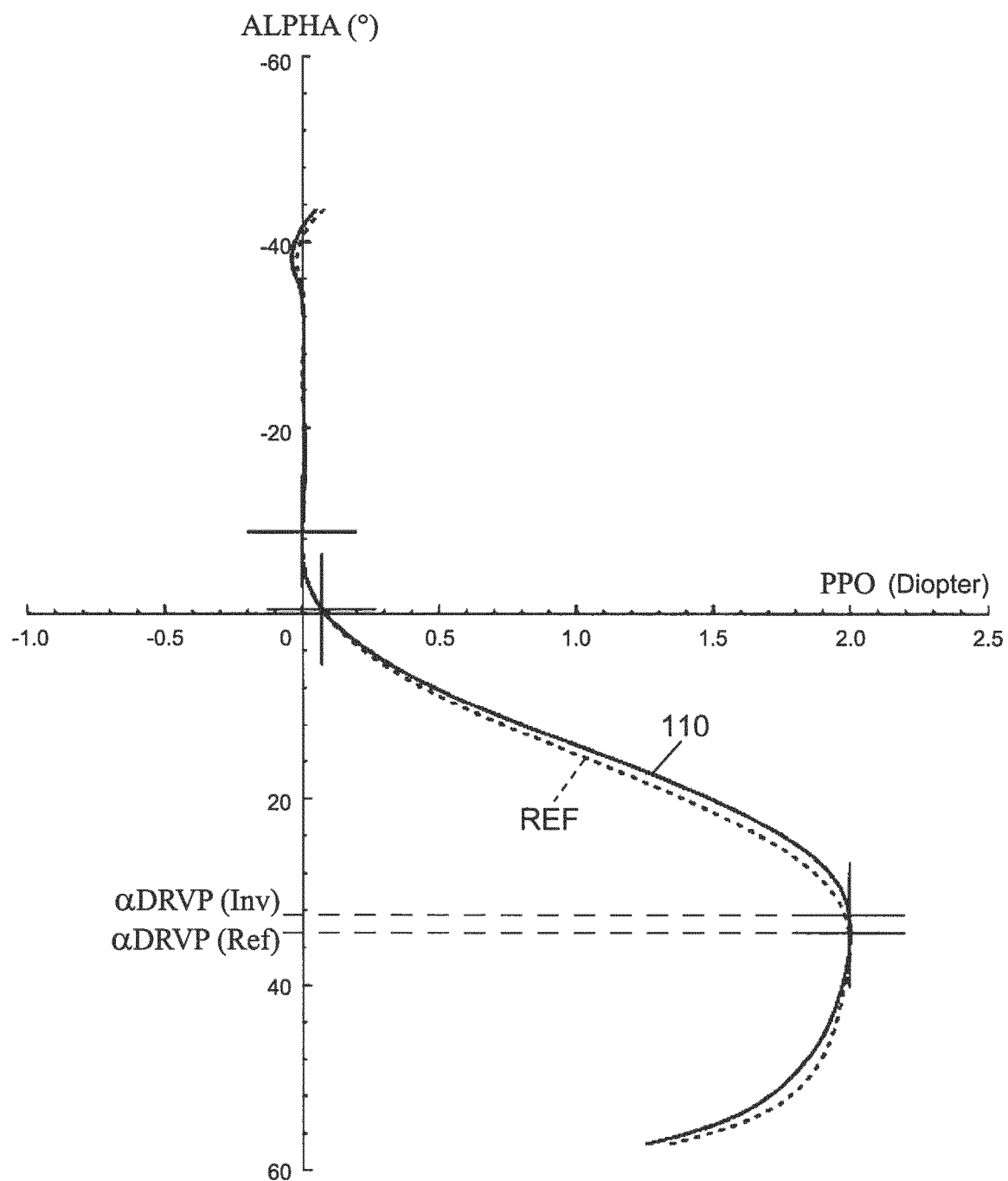
FIGS. 11 to 19 represent the optical properties of three progressive lenses obtained by virtue of the method of the present invention compared with those of a reference progressive lens.
Figure 14:
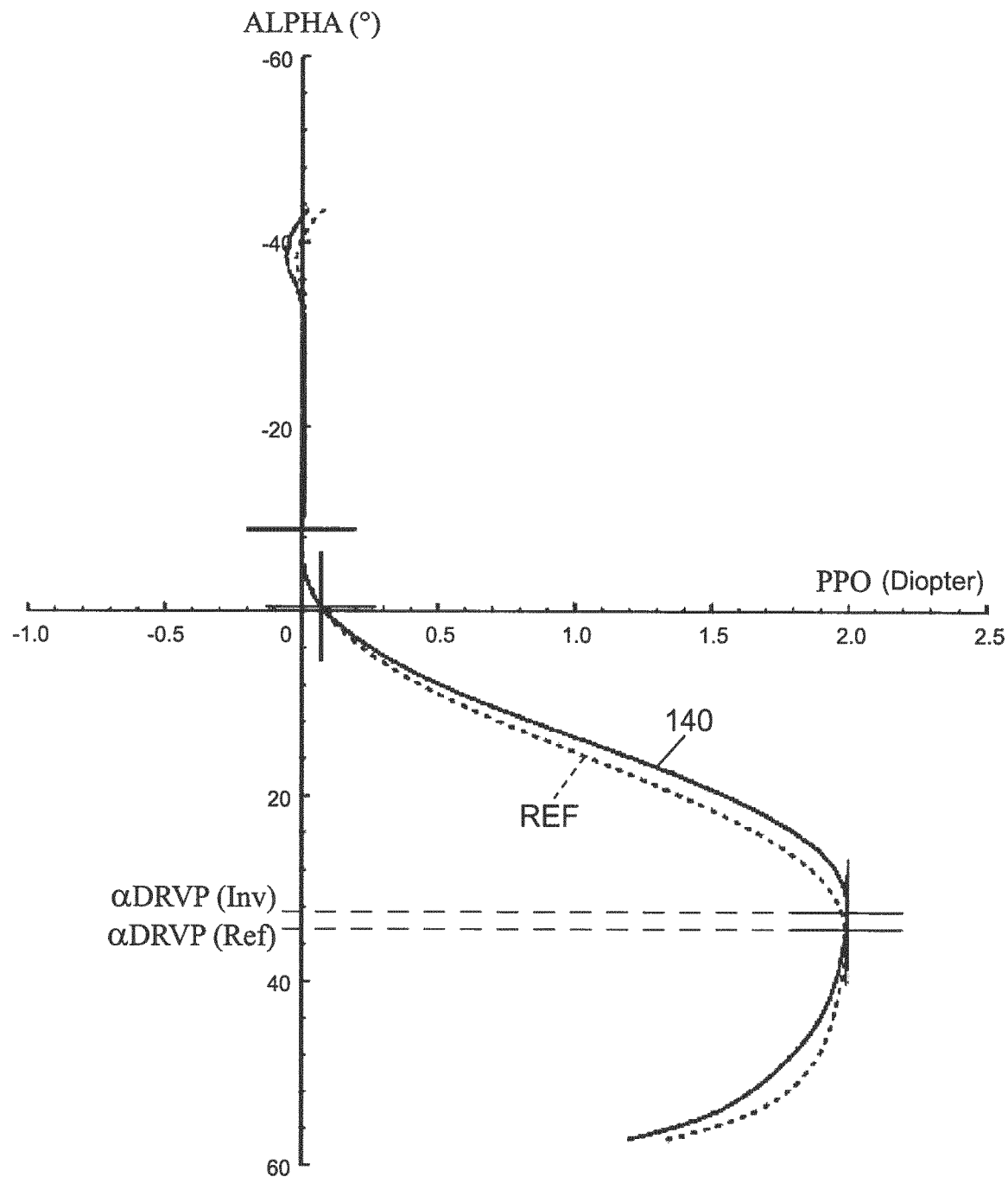
Figure 17:
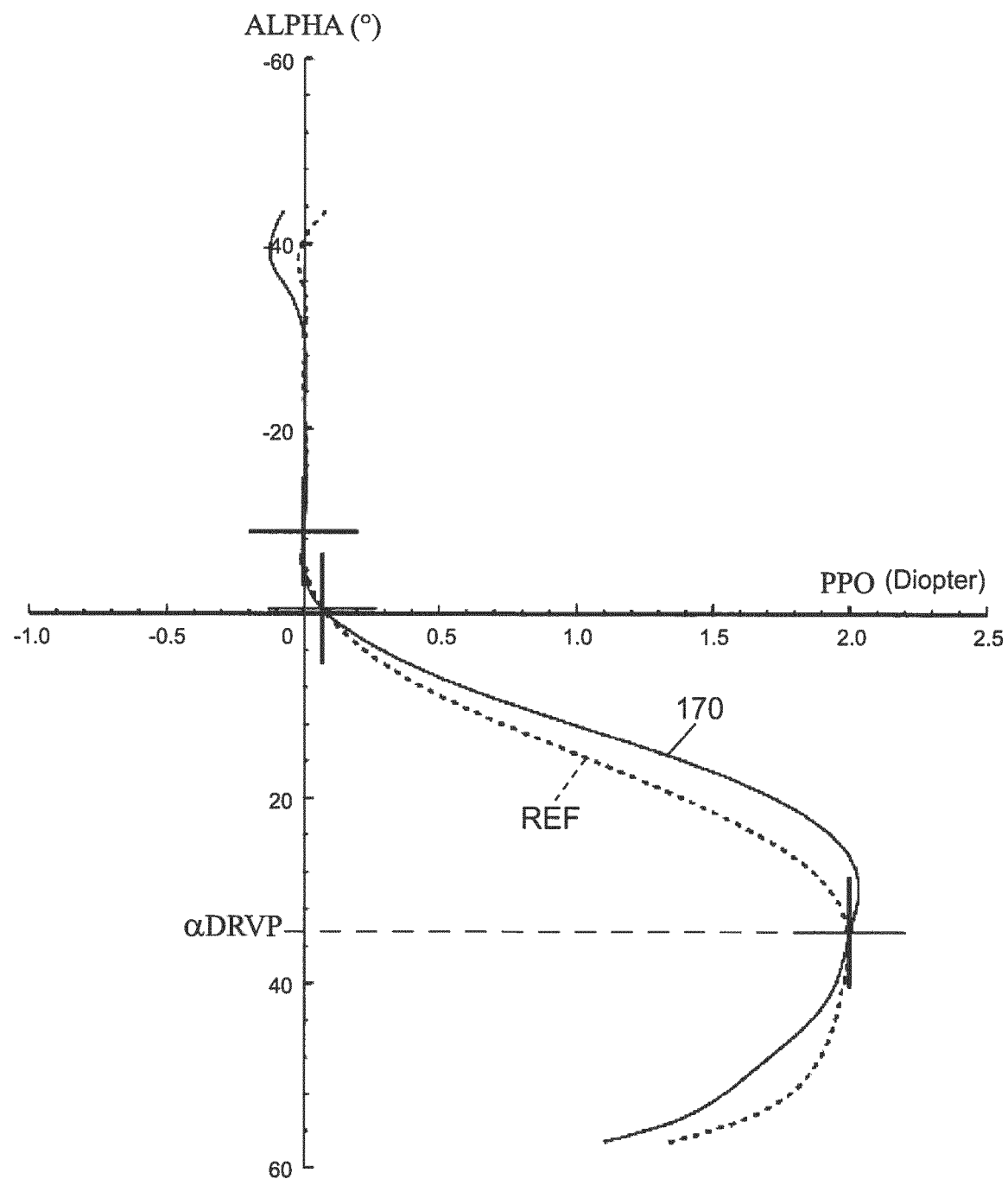

FIGS. 11, 14 and 17 represent profiles of distribution of the mean refractive power, PPO, along the meridian, as a function of the gaze lowering angle α, with, shown dotted, the profile corresponding to the reference lens and, shown solid, the profile corresponding to an example according to the present invention, corresponding respectively to curves 110, 140 and 170.

Figure 12:
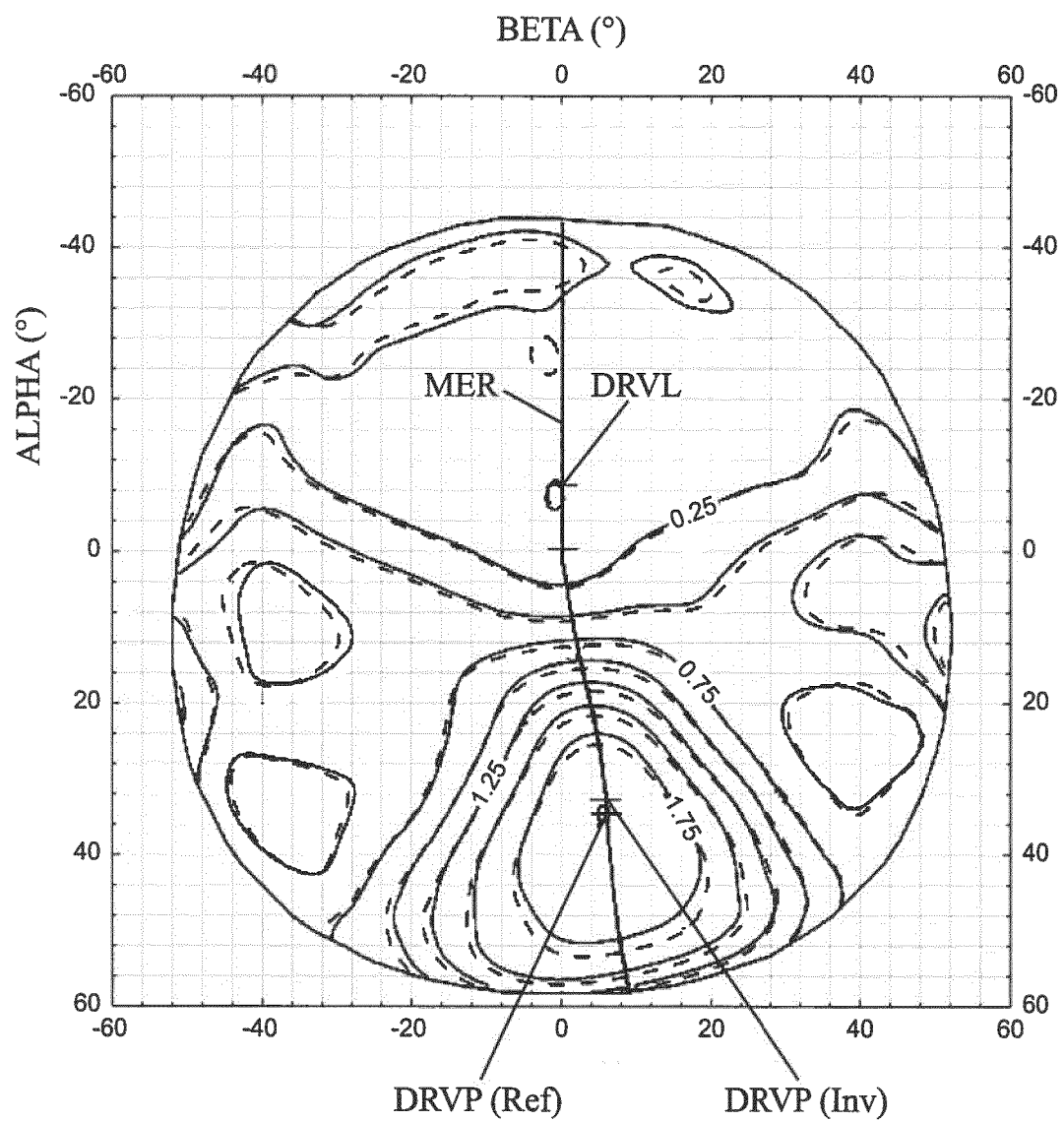
Figure 15:
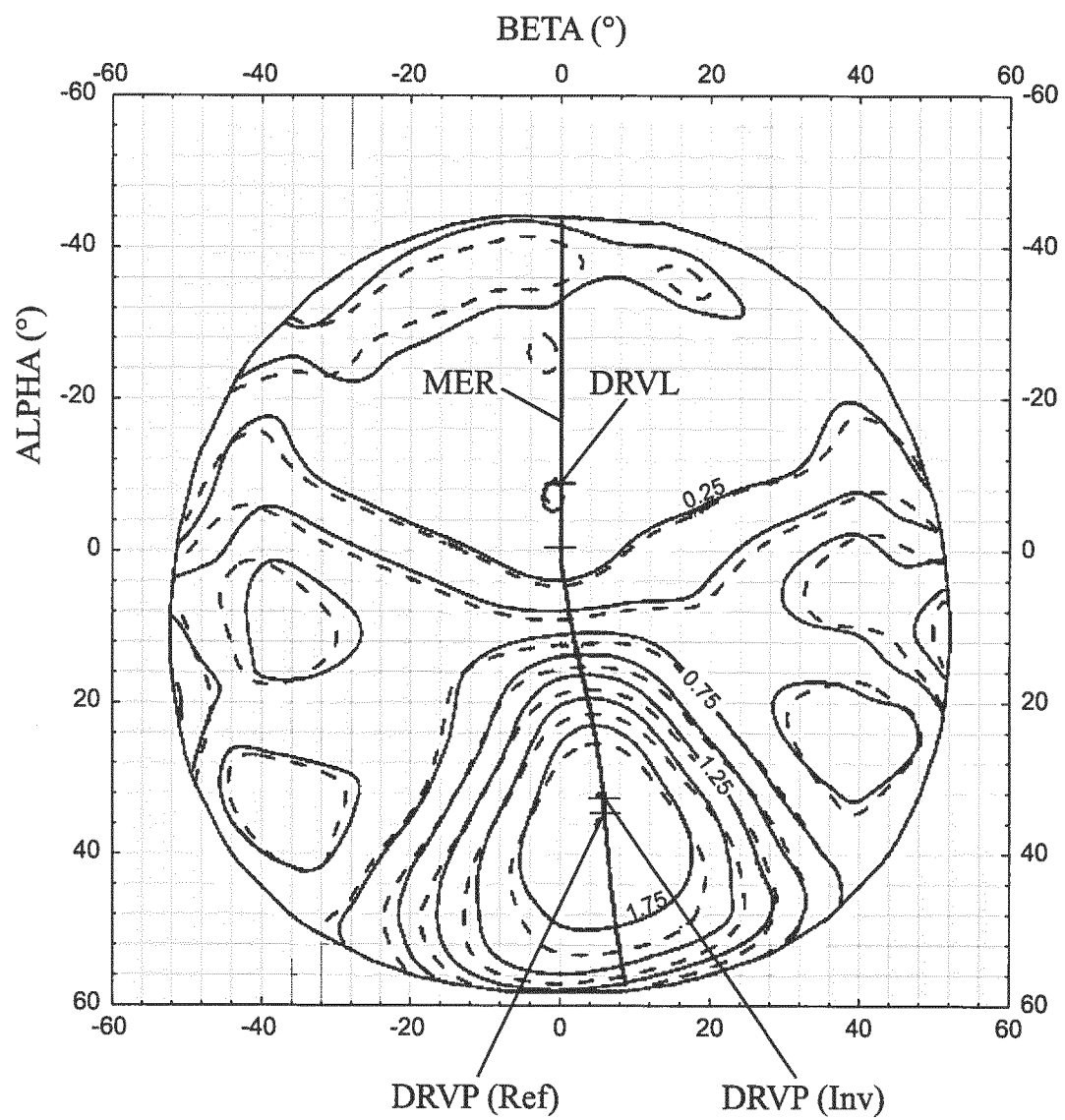
Figure 18:
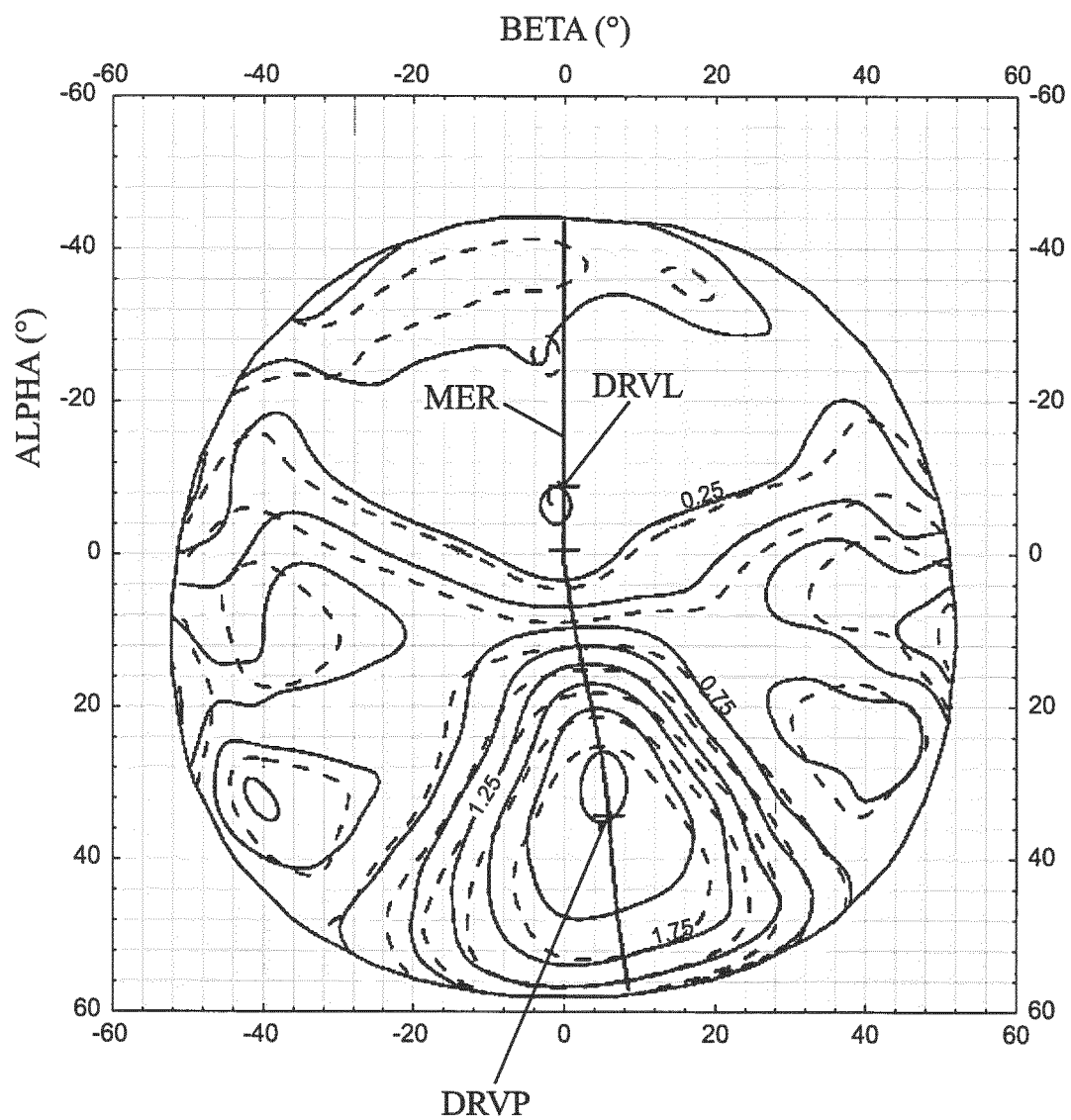

FIGS. 12, 15 and 18 represent curves of mean refractive power, PPO, in the form of iso-mean refractive power curve where the variation in mean refractive power between two neighbouring curves of different mean refractive power is 0.25 Diopters; the values of the curves of iso-mean refractive power are indicated every 0.50 diopters and the values of the curves of iso-mean refractive power without indication correspond to the mean of the two neighbouring curves. The curves of mean refractive power are represented over the domain (α, β), with, shown dotted, the curves corresponding to the reference lens and, shown solid, the curves corresponding to an example according to the present invention.

Figure 13:
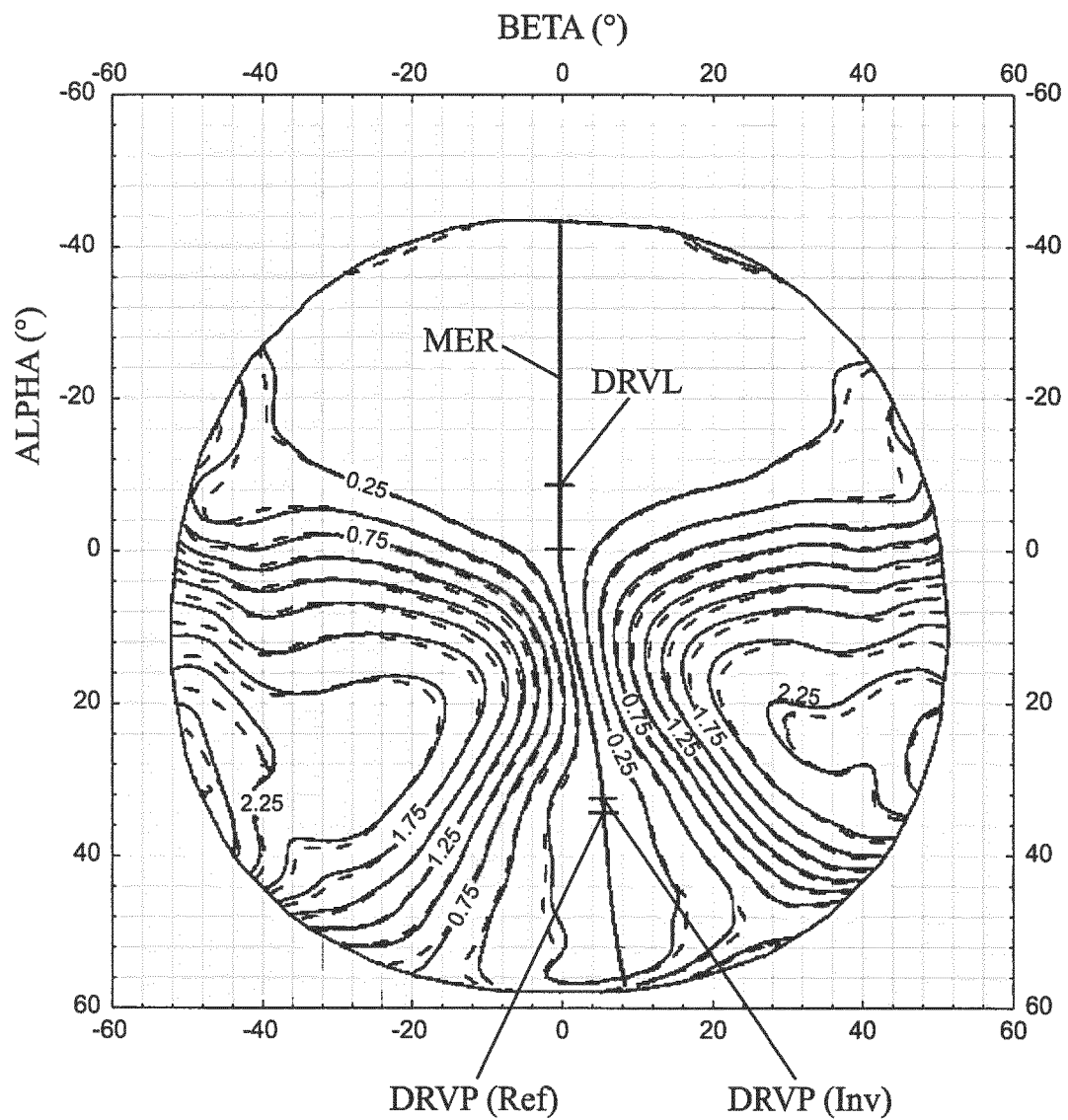
Figure 16:
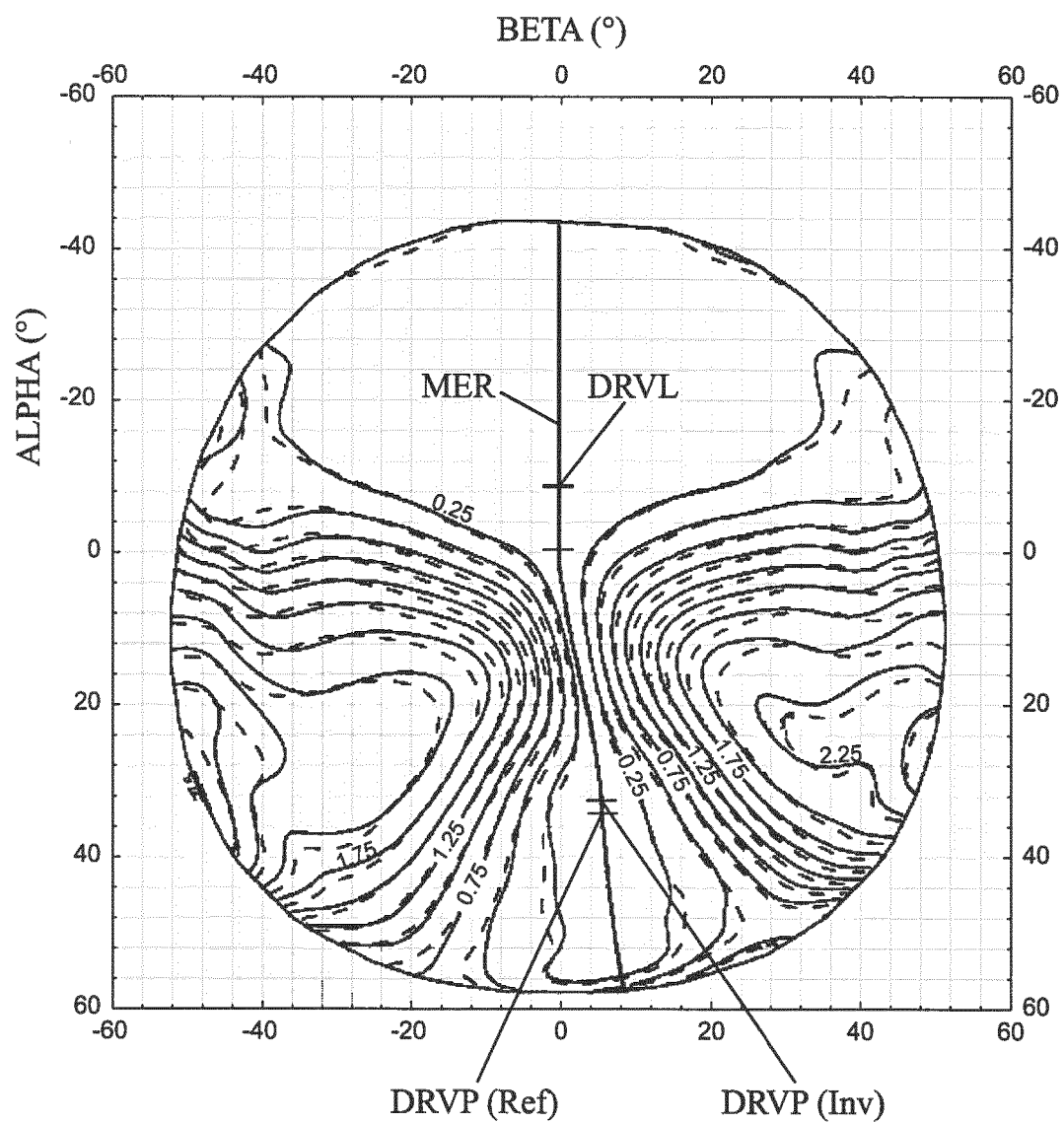
Figure 19:
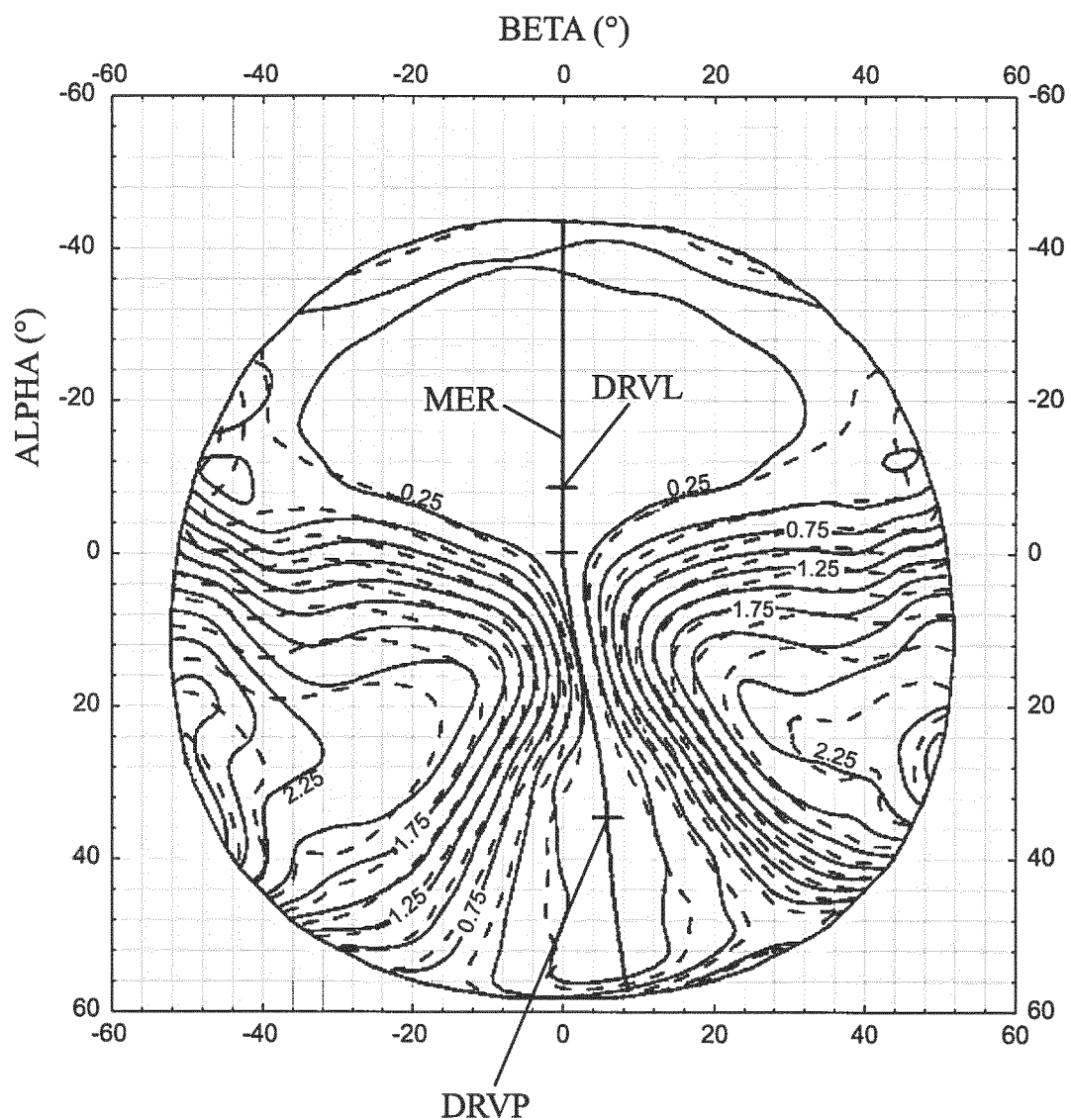

FIGS. 13, 16 and 19 represent curves of resulting astigmatism, ASR, in the form of iso-resulting astigmatism curve where the variation in resulting astigmatism between two neighbouring curves of different mean refractive power is 0.25 Diopters; the values of the curves of resulting astigmatism are indicated every 0.50 diopters and the values of the curves of resulting astigmatism without indication correspond to the mean of the two neighbouring curves. The curves of resulting astigmatism are represented over the domain (α, β), with, shown dotted, the curves corresponding to the reference lens and, shown solid, the curves corresponding to an example according to the present invention.

The concepts of "gaze lowering angle, α", of "azimuthal angle, β", of "domain (α, β)", of "mean refractive power, PPO", of "resulting astigmatism, ASR" are known to a person skilled in the art and in particular explained in patent document WO 2015/074777 A1, to which reference is made.

The optical properties of Example 1, Example 2, Example 3 correspond to the solid-line representations of FIGS. 11 to 13.

The optical properties of Example 4 correspond to the solid-line representations of FIGS. 14 to 16.

The optical properties of Example 5 correspond to the solid-line representations of FIGS. 17 to 19.

FIGS. 11 to 19 in conjunction with Examples 1 to 5 are indeed of such a nature as to demonstrate that the method for determining an optical system of a progressive lens according to the present invention is of such a nature as to allow an advantageous personalization for a given wearer.

The invention claimed is:

1. A method for determining an optical system of a progressive lens defined at least by a fitting cross, the progressive lens being personalized for a given wearer having prescription data, including a prescribed addition, and the method being implemented by a computer processor and comprising:

a) providing a mean direction of gaze determined for a plurality of gaze directions of the wearer in a reference frame-tied to the head of the wearer;

b) determining a target value for at least one optical design parameter as a function of the mean direction of gaze-determined in a);

c) calculating the optical system of the progressive lens for the wearer by an optical optimization procedure based on target values, wherein the prescription data are target values of the calculation and wherein the target value of each optical design parameter as a function of the mean direction of gaze determined in b) is a supplementary target value of the calculating of the optical system, wherein providing the mean direction of gaze originates from a result of a procedure comprising:

requesting the wearer to perform a visual test in a course of which the wearer observes at least one target position of an object;

measuring at least one datum representative of a plurality of directions of gaze of the wearer in the course of the visual test, wherein the directions of gaze are observation directions which correspond to straight lines linking a center of rotation of an eye of the wearer to a point of the object;

determining a mean direction of gaze, as a function of the at least one measured representative datum; and wherein in the procedure for providing the mean direction of gaze:

the wearer successively observes various target positions of the object;

directions of gaze of the wearer are determined in the course of the visual test in a reference frame tied to the head of the wearer;

coordinates of the target positions are determined in the reference frame tied to the head of the wearer;

a barycenter of the target positions in the reference frame tied to the head of the wearer is determined on the basis of the coordinates; and the mean direction of gaze is determined as a straight line linking a center of rotation of a left eye or right eye of the wearer, or a barycenter of the centers of rotation, to the barycenter of the target positions in the reference frame tied to the head of the wearer; and positioning, with respect to the mean direction of gaze, at least one measured target position which is determined, in a reference frame tied to the head of the wearer, as a function of the datum representative of the direction of gaze of the wearer, corresponding to the observation direction, measured in the course of the visual test.

2. The method according to claim 1, wherein the optical design parameter of b) is a personalized progression length chosen from among a personalized total progression length and a personalized partial progression length.

3. The method according to claim 2, wherein the optical design parameter of b) is a personalized total progression length and wherein the target value of personalized total progression length is defined by the difference between the fitting cross and a point corresponding to a projection of the mean direction of gaze-in the plane of the lens.

4. The method according to claim 3, wherein an additional target value defined as a value of a personalized partial progression length is introduced into c) of calculating the optical system of the progressive lens for the wearer.

5. The method according to claim 4, wherein the value of the personalized partial progression length is a result of a transfer function having as a variable a visual behavior parameter of the wearer.

6. The method according to claim 2, wherein the optical design parameter of b) is a personalized total progression length and wherein the target value of the personalized total progression length is defined by the difference between the fitting cross and a point corresponding to the result of a transfer function having as a variable the point corresponding to a projection of the mean direction of gaze-in the plane of the lens.

7. The method according to claim 6, wherein an additional target value defined as a value of a personalized partial progression length is introduced into c) of calculating the optical system of the progressive lens for the wearer.

8. The method according to claim 7, wherein the personalized partial progression length is defined by the difference between the fitting cross and a point corresponding to 85% of the prescribed addition.

9. The method according to claim 2, wherein the personalized partial progression length is defined by the difference between the fitting cross and a point corresponding to 85% of the prescribed addition.

10. The method according to claim 1, wherein in the procedure for providing the mean direction of gaze:
the mean direction of gaze is determined as a straight line linking a center of rotation of the left eye or right eye of the wearer, or a barycenter of the centers of rotation, to a target position in the reference frame tied to the head of the wearer.

11. The method according to claim 1, wherein the visual behavior parameter of an individual is provided in the course of the procedure for providing the mean direction of gaze, in the course of which the visual behavior parameter of the individual is furthermore determined according to:

positioning, with respect to the mean direction of gaze, theoretical target positions whose relative dispositions with respect to one another are identical to the relative dispositions of the target positions;

during the visual test, the target positions are disposed on a display surface, and, during the positioning, a dummy display surface oriented, with respect to the reference direction of gaze, according to a mean orientation of the display surface during the visual test is determined and the measured target positions are determined as the intersections of the directions of gaze of the wearer in the course of the visual test and of the dummy display surface;

differences are determined between the theoretical target positions and the measured target positions according to a favored direction of the dummy surface and the visual behavior parameter of the wearer is deduced therefrom.

12. The method according to claim 11, wherein deduction of the visual behavior parameter is performed as a function of a statistical processing of the differences between the theoretical target positions and the measured target positions.

13. The method according to claim 11, wherein the method further comprises positioning of the theoretical target positions so that the barycenter of the theoretical target positions lies on the reference direction of gaze.

14. The method for manufacturing a progressive lens by machining of a semi-finished lens according to results of the calculation of the optical system of the progressive lens for the wearer of claim 1.

15. A non-transitory computer readable medium comprising a computer program comprising a plurality of recorded sequences accessible to a processor and which, when executed by the processor implements the method according to claim 1.

* * * * *